United States Patent
Chaparro Padilla et al.

(10) Patent No.: US 11,009,512 B2
(45) Date of Patent: May 18, 2021

(54) IN VITRO METHOD FOR IDENTIFYING A PREGNANCY RELATED DISEASE

(71) Applicant: UNIVERSIDAD DE LOS ANDES, Las Condes (CL)

(72) Inventors: Alejandra Chaparro Padilla, Las Condes (CL); Sebastian Illanes Lopez, Las Condes (CL)

(73) Assignee: UNIVERSIDAD DE LOS ANDES, Santiago (CL)

( * ) Notice: Subject to any disclaimer, the term of this patent is extended or adjusted under 35 U.S.C. 154(b) by 36 days.

(21) Appl. No.: 15/758,706

(22) PCT Filed: Sep. 12, 2016

(86) PCT No.: PCT/IB2016/055426
§ 371 (c)(1),
(2) Date: Mar. 8, 2018

(87) PCT Pub. No.: WO2017/042751
PCT Pub. Date: Mar. 16, 2017

(65) Prior Publication Data
US 2018/0259534 A1 Sep. 13, 2018

Related U.S. Application Data

(60) Provisional application No. 62/217,270, filed on Sep. 11, 2015.

(30) Foreign Application Priority Data

Mar. 21, 2016 (EP) .................... 16161490

(51) Int. Cl.
*G01N 33/68* (2006.01)
*G01N 33/53* (2006.01)

(52) U.S. Cl.
CPC ....... *G01N 33/689* (2013.01); *G01N 2333/71* (2013.01); *G01N 2800/042* (2013.01); *G01N 2800/368* (2013.01)

(58) Field of Classification Search
None
See application file for complete search history.

(56) References Cited

FOREIGN PATENT DOCUMENTS

| JP | 2009-511911 A | 3/2009 | |
|---|---|---|---|
| WO | WO-2005017192 A2 * | 2/2005 | ........... G01N 33/689 |
| WO | WO 2006/069373 A2 | 6/2006 | |
| WO | WO 2014/142752 A1 | 9/2014 | |

OTHER PUBLICATIONS

Bashiri et al. Arch Gynecol Obstet (2007) 275:211-214 (Year: 2007).*
Mitchell et al. American Journal of Obstetrics & Gynecology 2015, S175 (Year: 2015).*
Orozco et al. Placenta. Oct. 2009 ; 30: 891-897 (Year: 2009).*
Canakci et al., "Total Antioxidant Capacity and Antioxidant Enzymes in Serum, Saliva, and Gingival Crevicular Fluid of Preeclamptic Women With and Without Periodontal Disease", Journal of Periodontology, 2007, 78(8): 1602-1611.
Chaparro et al., "Increased inflammatory biomarkers in early pregnancy is associated with the development of pre-eclampsia in patients with periodontitis: a case control", Journal of Periodontal Research, 2013, 48(3): 302-307.
Chaparro et al., "Placental biomarkers and angiogenic factors in oral fluids of patients with preeclampsia", Prenatal Diagnosis, 2016, 36(5): 476-482.
Dasanayake et al., "The association between Porphyromonas gingivalis-specific maternal serum IgG and low birth weight", J Periodontol, 2001, 72(11): 1491-1497.
Eleftheriades et al., "Elevated placental growth factor concentrations at 11-14 weeks of gestation to predict gestational diabetes mellitus", Metabolism, 2014, 63(11): 1419-1425.
Feig et al., "Diabetes in pregnancy outcomes: A systematic review and proposed codification of definitions", Diabetes Metab Res Rev., 2015, 31: 680-690.
Gumus et al., "Evaluation of Biochemical Parameters and Local and Systemic Levels of Osteoactive and B-Cell Stimulatory Factors in Gestational Diabetes in the Presence or Absence of Gingivitis", Journal of Periodontology, 2015, 86(3): 387-397.
Ha et al., "Oral Health Behaviors, Periodontal Disease, and Pathogens in Preeclampsia: A Case-Control Study in Korea", Journal of Periodontology, 2011, 82(12): 1685-1692.
Li et al., "Impaired proliferation of pancreatic beta cells, by reduced placental growth factor in pre-eclampsia, as a cause for gestational diabetes mellitus", Cell Proliferation, 2015, 48(2): 166-174.
Oettinger-Barak et al., "Severe pregnancy complication (preeclampsia) is associated with greater periodontal destruction", Journal of Periodontology, 2005, 76(1): 134-137.
Yu et al., "Anti-angiogenic factors and pre-eclampsia in type 1 diabetic women", Diabetologia, 2008, 52: 160-168.
Ronin-Walknowska et al., "Placental Alkaline Phosphatase Compared with Human Placental Lactogen and Oestriol in High-Risk Pregnancies", Gynecol. Obstet. Invest., 1984, 18: 206-211.

* cited by examiner

*Primary Examiner* — Changhwa J Cheu
(74) *Attorney, Agent, or Firm* — James S. Keddie; Bozicevic, Field & Francis LLP

(57) ABSTRACT

The present invention is focused on an in vitro method for identifying or screening human subjects at risk of suffering from a pregnancy related disease, in particular from gestational diabetes mellitus or preeclampsia, departing from the level of expression or concentration of a series of biomarkers isolated from a minimally-invasive sample such as gingival crevicular fluid (GCF). Moreover, the method of the invention offers high sensitivity and specificity at an early stage of the pregnancy (see the Examples and figures shown below), which means that it is a strong and cost-effective method for the detection of a pregnancy related disease, in particular gestational diabetes mellitus or preeclampsia, at an early stage of the disease thus procuring effective treatment, avoiding significant long-term adverse effects for both mother and baby.

8 Claims, 17 Drawing Sheets

A)

B)

C)

D)

E)

F)

G)

A)

B)

C)

A)

B)

| PE | Crude O.R | p-value | 95% Conf. Interval |
|---|---|---|---|
| Severe Periodontitis | 9.362733 | 0.009 | 1.764856 - 49.67022 |

| PE | Adjusted O.R | p-value | 95% Conf. Interval | |
|---|---|---|---|---|
| Severe periodontitis | 7.671933 | 0.025 | 1.296962 | 45.38187 |
| Age (years) | 1.068504 | 0.389 | .9189598 | 1.242383 |
| Body mass index (BMI) | 1.052858 | 0.408 | .9320421 | 1.189334 |
| Tobacco history | 1.908239 | 0.425 | .3895946 | 9.346574 |

A)

B)

C)

D)

IN VITRO METHOD FOR IDENTIFYING A PREGNANCY RELATED DISEASE

CROSS-REFERENCE TO RELATED APPLICATIONS

This application is a § 371 national phase of International Application No. PCT/IB2016/055426, filed on Sep. 12, 2016, which claims the benefit of U.S. Provisional Application No. 62/217,270, filed on Sep. 11, 2015, and European Application No. 16161490.4, filed on Mar. 21, 2016, all of which applications are incorporated by reference herein.

FIELD OF THE INVENTION

The present invention can be included in the field of personalized medicine, wherein specific biomarkers are used for identifying a given disease or disorder. Specifically, some biomarkers are used in the present invention for identifying human subjects at risk of developing maternal gestational diabetes mellitus or preeclampsia.

PRIOR ART

Maternal gestational diabetes mellitus (GDM) occurs in approximately 7% of pregnancies, and is a multifactorial disease that has been linked with infection and systemic inflammation among others risk factors (The association between Porphyromonas gingivalis-specific maternal serum IgG and low birth weight. Dasanayake A P, Boyd D, Madianos P N, Offenbacher S, Hills E. J Periodontol. 2001 November; 72(11): 1491-7.). GDM is defined as glucose intolerance with onset or first recognition during pregnancy (International Association of Diabetes in Pregnancy Study Group Working Group on Outcome D, Feig D S, Corcoy R, Jensen D M, Kautzky-Willer A, Nolan C J, et al. Diabetes in pregnancy outcomes: A systematic review and proposed codification of definitions. Diabetes Metab Res Rev. 2015). It is a form of diabetes that appears during pregnancy and usually resolves after delivery. If left untreated, GDM can cause significant long-term adverse effects for both mother and baby. Perinatal morbidity includes hyperinsulinaemia, macrosomia, hypoglycaemia, hyperbilirubinaemia, and respiratory distress syndrome, which in turn may generate subsequent complications. Longer-term morbidity for the offspring includes obesity and diabetes independent of genetic factors. Furthermore, GDM in the mother is associated with a 70% lifetime risk of developing Type II diabetes.

The present invention confronts the problem of providing a new method for identifying pregnant female subjects, in particular women, at risk of developing gestational diabetes mellitus as early as possible during the pregnancy in order to avoid long-term adverse effects for both mother and baby.

In addition, Preeclampsia (PE) is a multi-organ disease that affects approximately 3 to 8% of pregnant women worldwide. Recent evidence indicates that administration of low-dose aspirin before weeks of gestation in patients at moderate or high risk to develop PE is associated with a reduction in the risk of PE, intrauterine growth restriction, preterm birth, and perinatal death. The current "gold standard" for the diagnosis of PE is done in second half of pregnancy (>of 24 weeks of gestation)" when the pathology is already established and the possibilities to reverse or limit the potential adverse effects on perinatal outcomes is limited. PE is the leading cause of both maternal and infant mortality during pregnancy.

There is thus a need for earlier diagnosis with accurate prediction of PE, for a precise identification and advance patient risk stratification and for effective therapeutic interventions and monitoring of PE.

BRIEF DESCRIPTION OF THE INVENTION

The present invention offers a clear solution to the problems cited above because it is focused on an in vitro method for identifying or screening human subjects at risk of suffering from a pregnancy related disease, in particular from gestational diabetes mellitus or preeclampsia, departing from the level of expression or concentration of a series of biomarkers isolated from a minimally-invasive sample such as gingival crevicular fluid (GCF). Moreover, the method of the invention offers high sensitivity and specificity at an early stage of the pregnancy (see the Examples and figures shown below), which means that it is a strong and cost-effective method for the detection of a pregnancy related disease, in particular gestational diabetes mellitus or preeclampsia, at an early stage of the disease thus procuring effective treatment, avoiding significant long-term adverse effects for both mother and baby.

DETAILED DESCRIPTION OF THE INVENTION

Definitions

Figure 1:
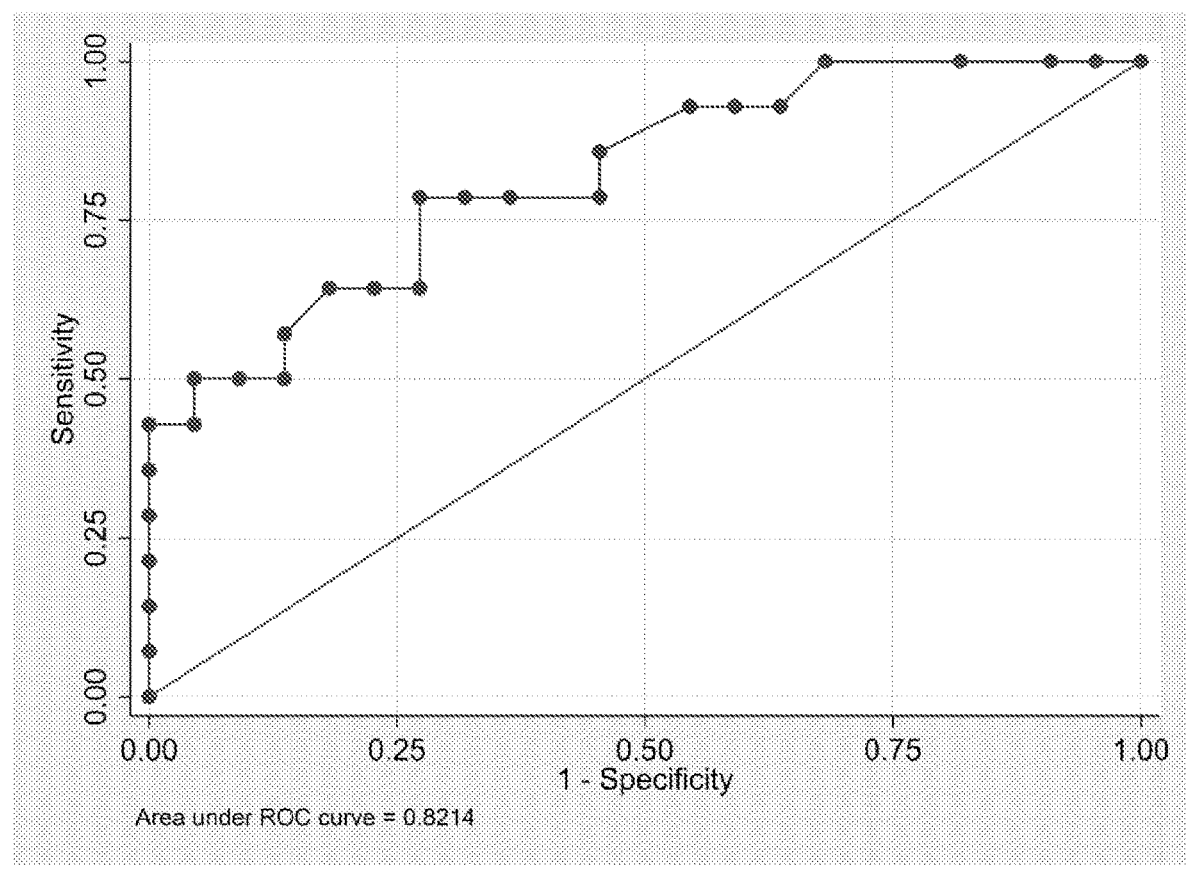
FIG. 1. Receiver Operating Characteristic curve of glycemia versus gestational diabetes status.

For the purpose of the present invention, the following definitions are included below:

The term "screening" is understood as the examination or testing of a group of individuals pertaining to the general population, at risk of suffering from gestational diabetes mellitus, with the objective of discriminating healthy individuals from those who are suffering from an undiagnosed gestational diabetes mellitus or who are at high risk of suffering from said indication.

As used herein "gestational diabetes mellitus (GDM)" is defined as glucose intolerance with onset or first recognition during pregnancy.

The expression "Gingival crevicular fluid (GCF)" is an inflammatory exudate that can be collected at the gingival margin or within the gingival crevice.

The term "up-regulated" or "over-expressed" of any of the biomarkers or combinations thereof described in the present invention, refers to an increase in their expression level with respect to a given "threshold value" or "cutoff value" by at least 5%, by at least 10%, by at least 15%, by at least 20%, by at least 25%, by at least 30%, by at least 35%, by at least 40%, by at least 45%, by at least 50%, by at least 55%, by at least 60%>, by at least 65%>, by at least 70%, by at least 75%, by at least 80%, by at least 85%, by at least 90%, by at least 95%, by at least 100%, by at least 110%, by at least 120%, by at least 130%, by at least 140%, by at least 150%, or more.

The term "threshold value" or "cutoff value", when referring to the expression levels of the biomarkers described in the present invention, refers to a reference expression level indicative that a subject is likely to suffer from gestational diabetes mellitus with a given sensitivity and specificity if the expression levels of the patient are above said threshold or cut-off or reference levels.

The term "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

It is also noted that the term "kit" as used herein is not limited to any specific device and includes any device suitable for working the invention such as but not limited to microarrays, bioarrays, biochips or biochip arrays.

As used herein "Placental Growth Factor (PlGF)" is a member of the Vascular Endothelial Growth Factor (VEGF) family of growth factors involved in the regulation of angiogenesis. PlGF is closely related to VEGF-A and binds to the VEGF receptor 1 (VEGFR-1, also known as soluble fms-Like Tyrosine Kinase 1, sFlt-1).

As used herein GDM diagnosis is confirmed by performing an oral glucose tolerance test (OGTT) at 24-28 weeks of gestation.

As used herein women were diagnosed with periodontitis if four or more teeth showed one or more sites with a probing pocket depth (PPD) of 4 mm or higher, as well as if they had a clinical attachment loss (CAL) of 3 mm or higher at the same site, inflammation and bleeding on probing (BOP). Women who showed BOP at more than 20% of the sites and gingival redness, but did not have clinical attachment loss, were diagnosed as having gingivitis.

As used herein "Glycemia" means the presence, or the level, of glucose in one's blood or serum.

As used herein the term "pregnancy-related-diseases" means diseases that are proper of pregnancy such as preterm birth, preeclampsia, gestational diabetes, etc.

As used herein the term "exosomes" means a subtype of nanovesicles, are a subtype of secreted cup-shaped membrane vesicles (30-100 nm) derived from late endosomal compartments and secreted from almost all cell types and tumor cells.

As used herein the term "micro-vesicles" means, membrane vesicles larger than 100-200 nm.

As used herein the term "sFlt-1 (antiangiogenic factor sFlt-1)" means a protein called fms-like tyrosine kinase-1 or a kind of soluble endothelial receptor.

As used herein the term "PLAP (placental alkaline phosphatase)" means a proteins specifically derived from the placenta, it is used for marked micro-vesices and exosomes of placental origin.

Description

The present invention refers to an in vitro method for screening or identifying subjects at risk of suffering from or having a pregnancy related disease, in particular gestational diabetes mellitus or preeclampsia, based on measuring the expression profile or level of some biomarkers which are up-regulated or over-expressed in patients suffering from this disease. The present invention also refers to an in vitro method for obtaining useful data for the diagnosis or for diagnosing a pregnancy related disease, in particular gestational diabetes mellitus or preeclampsia, in a subject, preferably in a human subject. Methods of treatment are also encompassed within the present invention.

Figure 8:
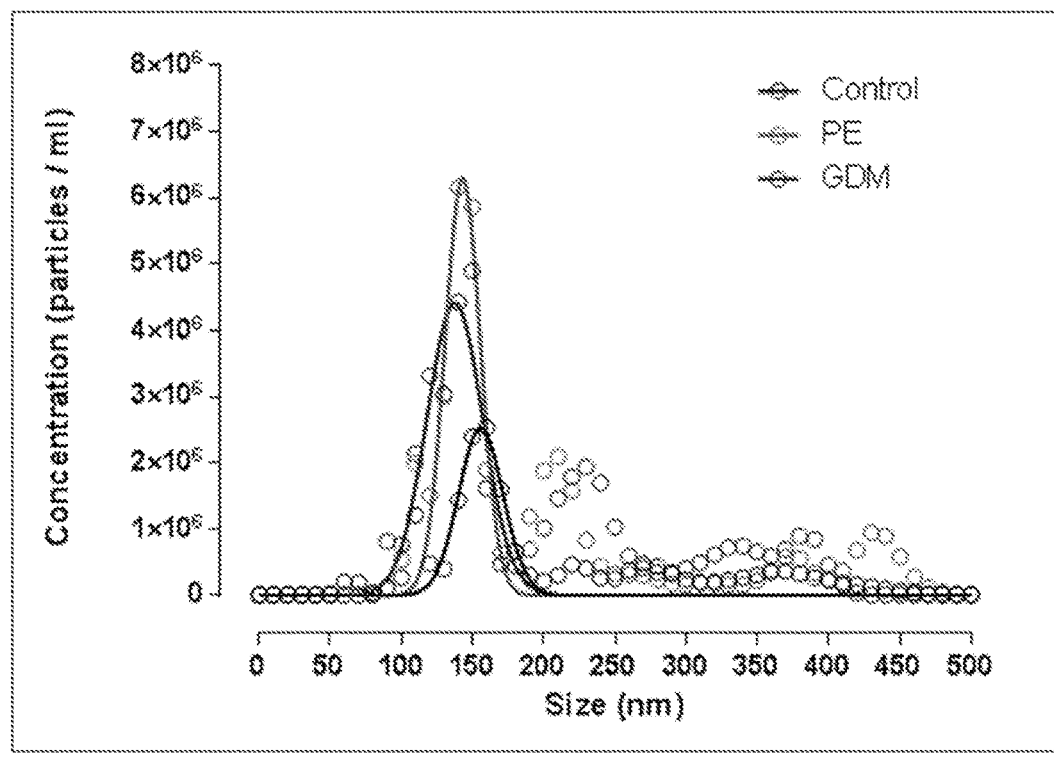
FIG. 8. A) Size distribution of extracellular vesicles (EVs) isolated from GCF (gingival crevicular fluid) from patients in the first trimester of pregnancy that developed gestational diabetes or PE vs healthy pregnancy (control). B) Quantificacion of EVs concentration in GCF from patients in the first trimester of pregnancy who developed GDM vs control. Nanotracking particles analysis. The size distribution of exosomes obtained will be analyzed using a NanoSight NS300 system (NanoSight) according to the manufacturer's instructions. Exosome samples isolated from hgMSCs, JEG-3 cells, and placental explants will be diluted in PBS prior analysis. The instrument will measure the rate of Brownian motion of nanoparticles, and the size distribution and concentration will be calculated.
Figure 8:
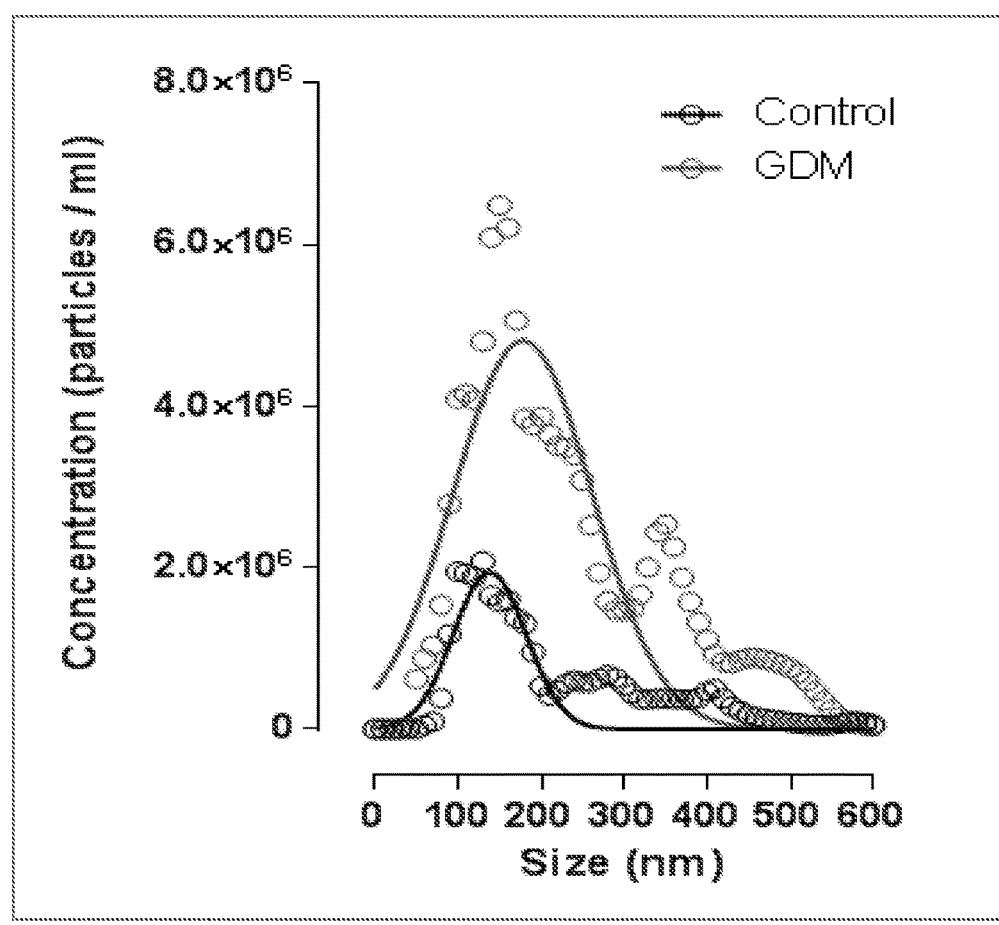
Figure 9:
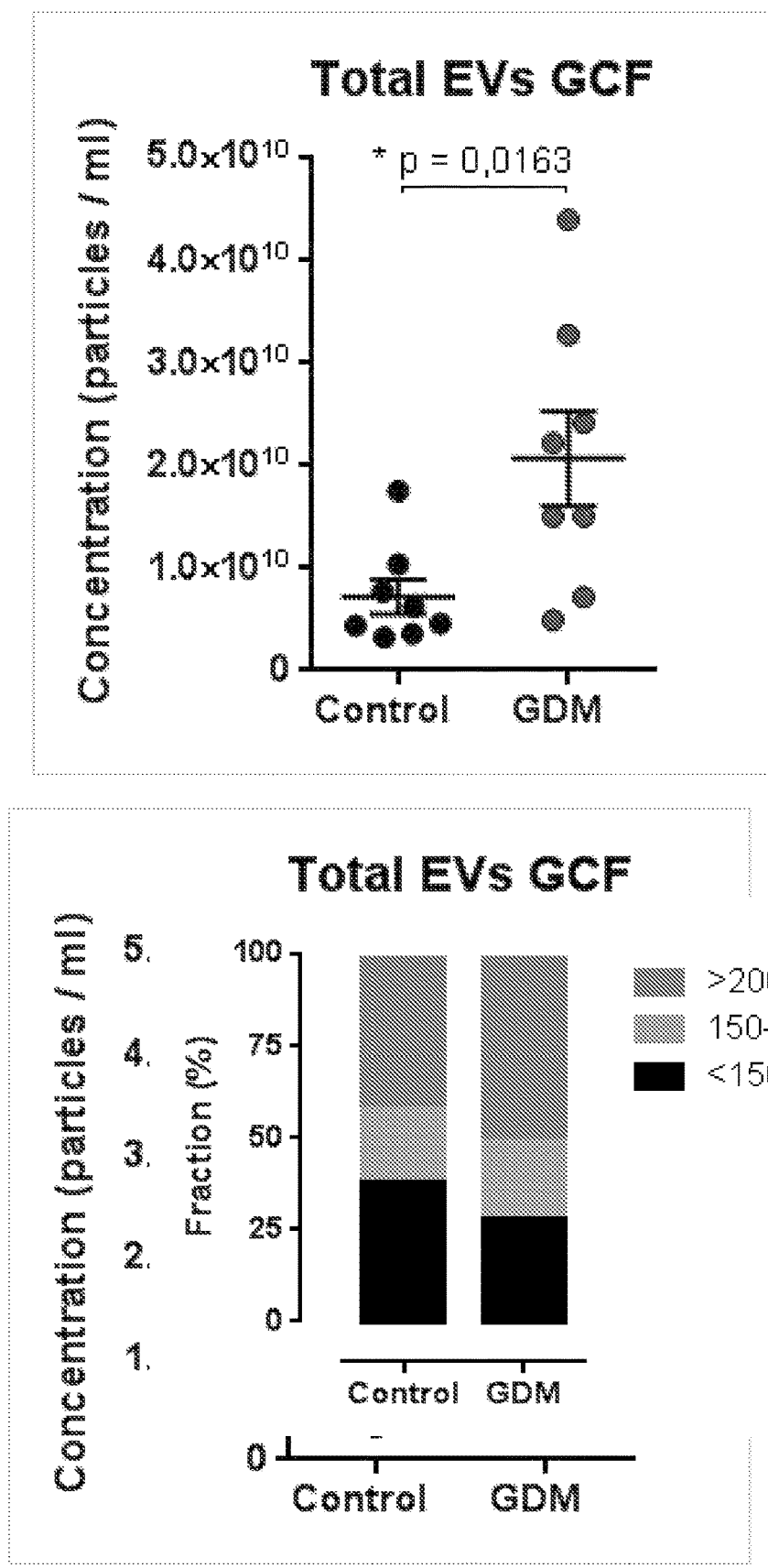
FIG. 9. Quantificacion of EVs concentration in GCF from patients in the first trimester of pregnancy who developed GDM n=12 vs control. n=17. P=0.0007.
Figure 10:
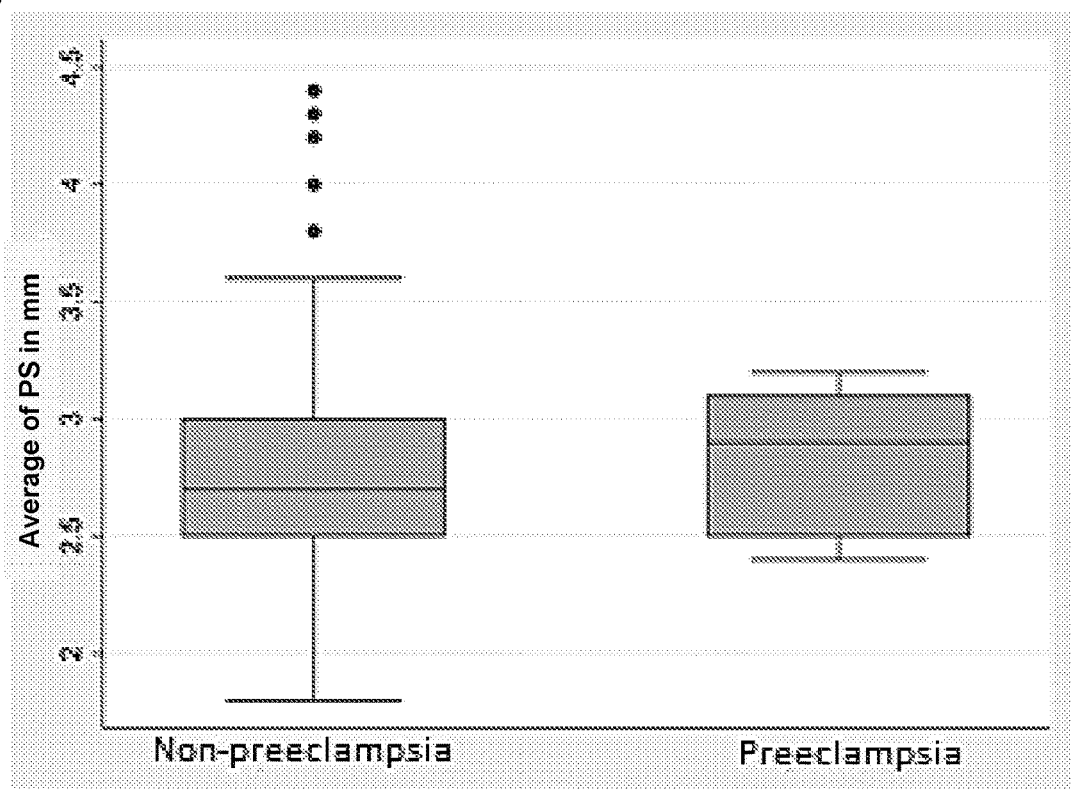
FIG. 10. A) Probing pocket depth measures at 11-14 weeks gestation in healthy and women who will develops preeclampsia. B) bleeding on probing (%) at 11-14 weeks gestation in healthy and women who will develops preeclampsia. C) Clinical attachment level at 11-14 weeks gestation in healthy and women who will develops preeclampsia.
Figure 10:
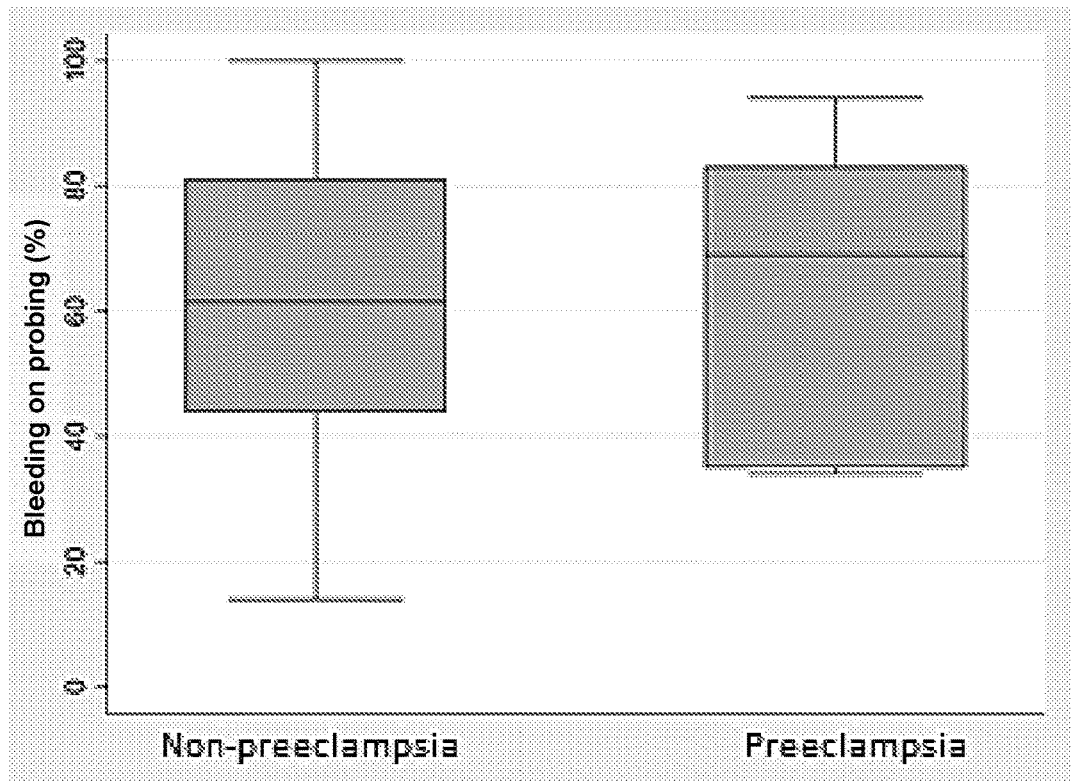
Figure 10:
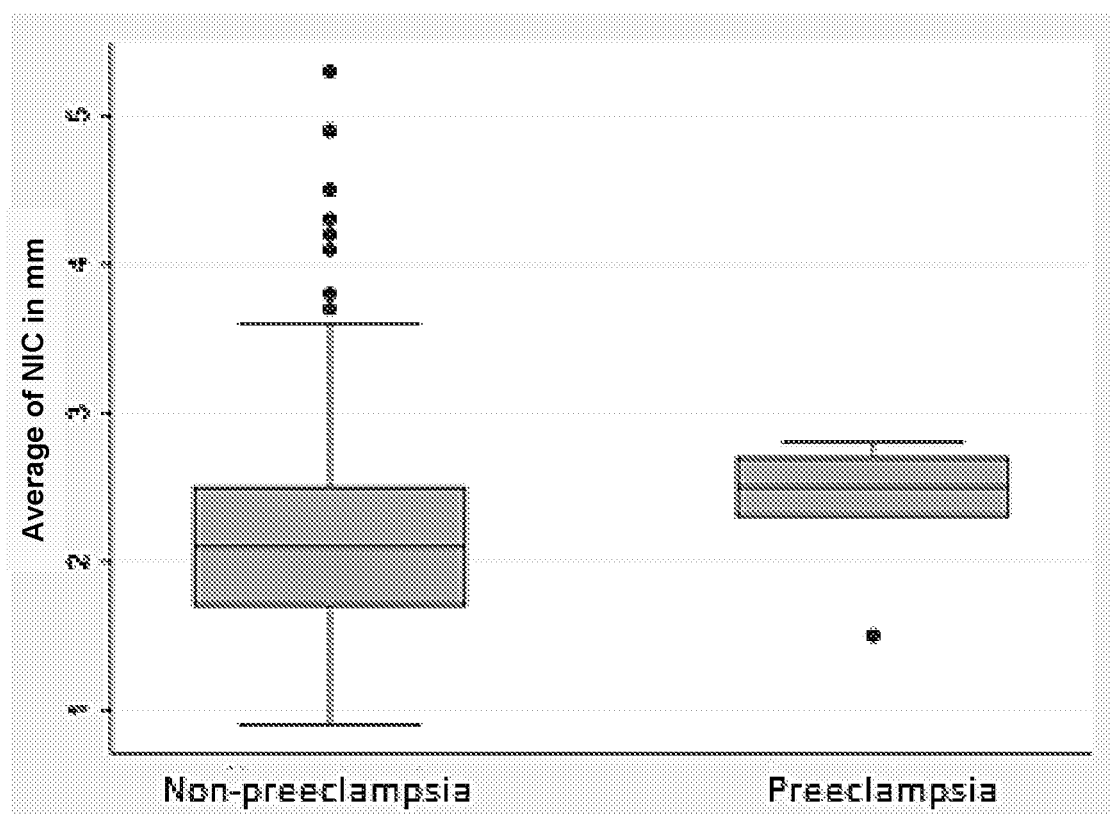
Figure 11:
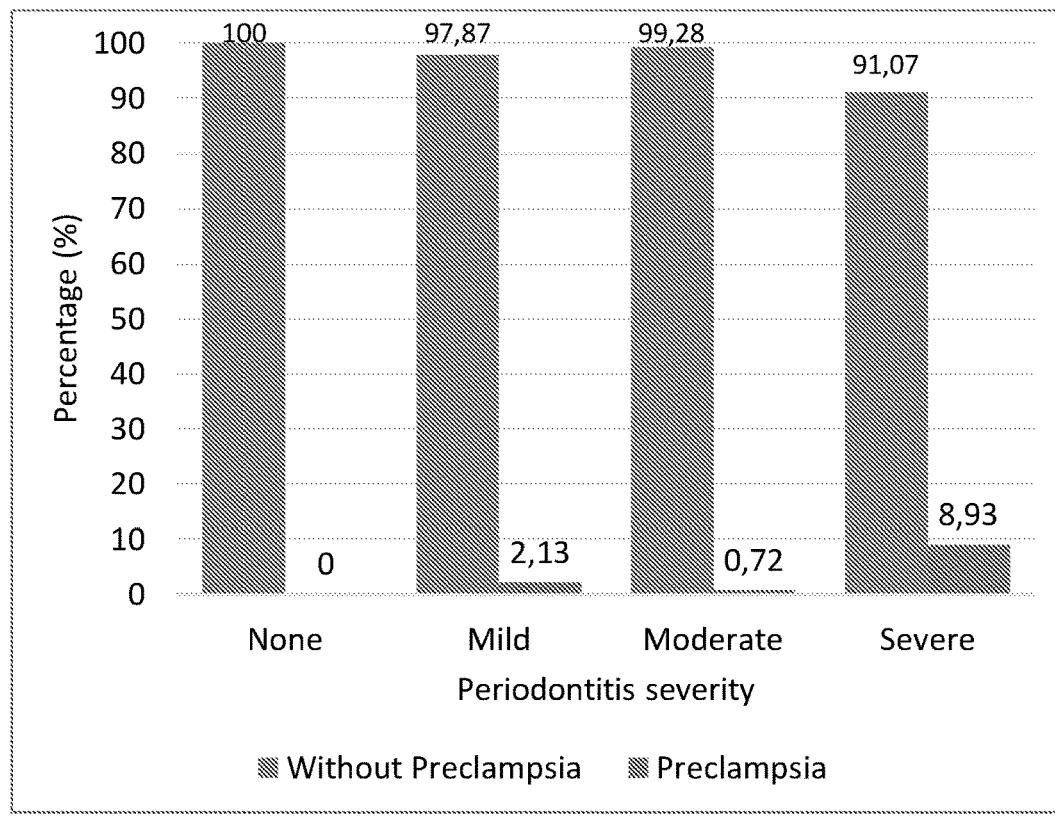
FIG. 11. A) Crude Odds ratio for the association between preeclampsia and severe periodontitis (O.R 9,36, p value=0.009). B) Adjusted regression model for the association between PE and Severe periodontitis, adjusted by age, tobacco use and body mass index.
Figure 12:
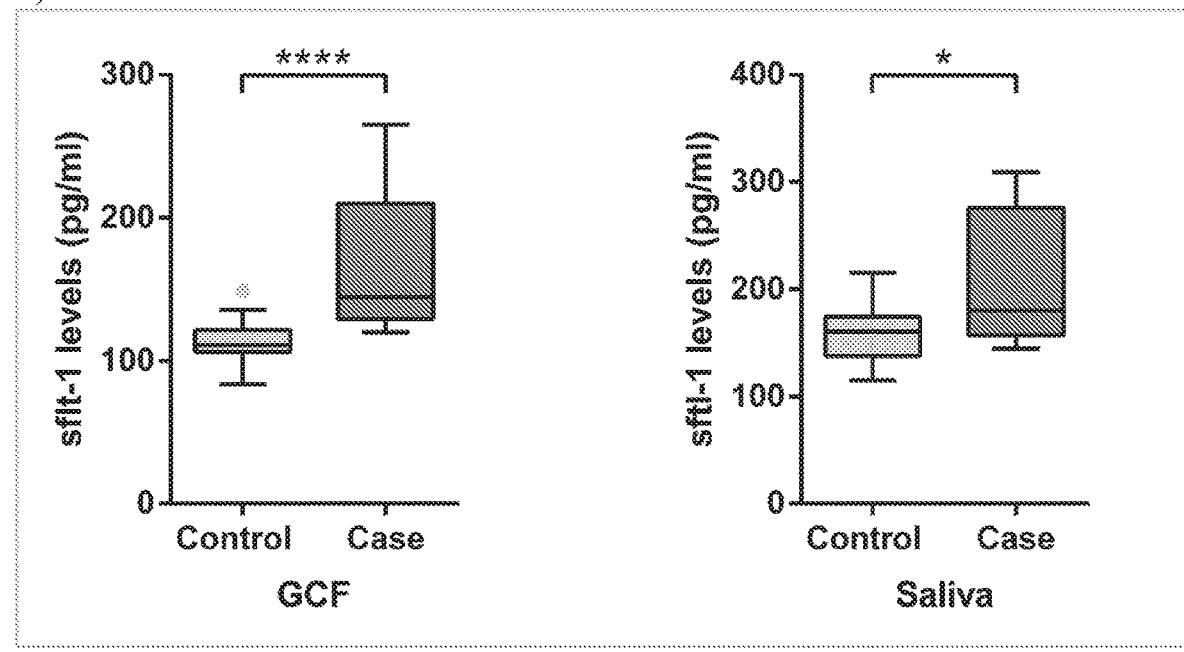
FIG. 12. A) Comparison of gingival crevicular fluid (GCF) and saliva sFlt-1 concentrations between woman with a normal pregnancy (control group) and preeclampsia (case group). The median maternal GCF and saliva sFlt-1 concentration was significantly increased in patients with preeclampsia (144.3 (p25-p75: 131.9-201.9) pg/ml and 180.5 pg/ml (p25-p75: 160.5-271.1) pg/ml), than those women with normal pregnancy (110.9 (p25-p75: 106.4-119.5) pg/ml and 160.5(p25-p75: 138.3-173) pg/ml). (p=0.033 and p=0.045 respectively). B) PLAP/EVs CD63+ ratio in maternal GCF and saliva in women with a normal pregnancy and preeclampsia. Patients with preeclampsia have a significantly higher maternal GCF PLAP/CD63+ ratio compared to normal pregnancy (p=0.0008). These results were not significant in maternal saliva. C) Comparison of gingival crevicular fluid (GCF) and saliva PlGF concentrations between women with a normal pregnancy (control group) and preeclampsia (case group). The median maternal GCF and saliva concentration of PlGF was not significantly different between both groups. Control group presented (17.9 (p25-p75: 11.3-39.4) pg/ml in GCF and 17.2 (p25-p75: 10.0-28.3) pg/ml in saliva), and preeclampsia patients (13.7 (p25-p75: 7.5-27.0) pg/ml in GCF and 16.9 (p25-p75: 4.8-29.6) pg/ml in saliva samples). D) Comparison of Maternal GCF and saliva PLAP concentrations between normal pregnancy (control group) and patients with preeclampsia (case group). GCF-PLAP concentrations were significantly higher in patients with preeclampsia in comparison with healthy pregnancies. The median maternal GCF-PLAP concentration was 1929.4 (p25-p75: 1915.4-2081.9) pg/ml in patients with preeclampsia, in comparison with women with normal pregnancy (1875.9 (p25-p75: 1844.0-1938.4) pg/ml). In saliva, no significant differences between groups were observed.
Figure 12:
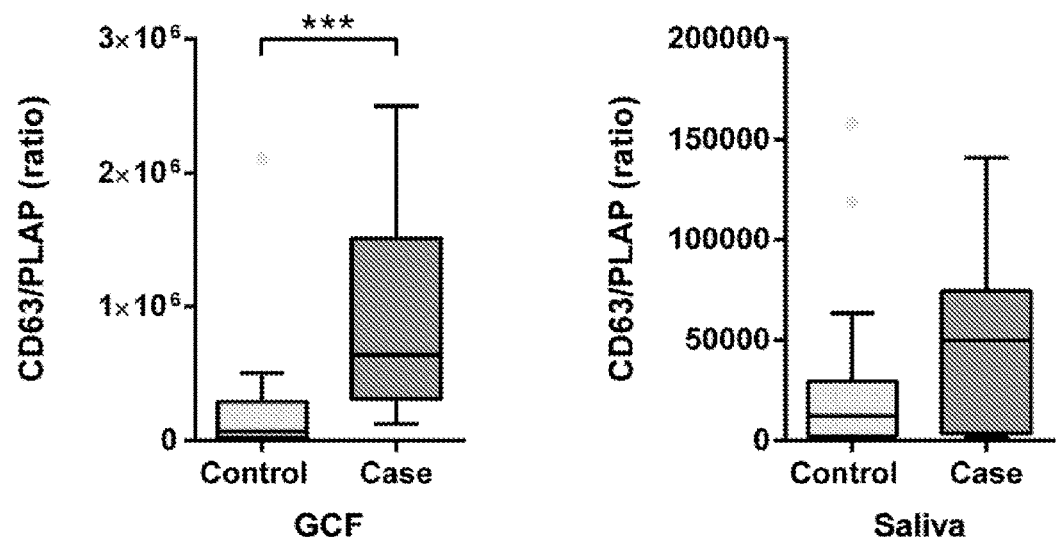
Figure 12:
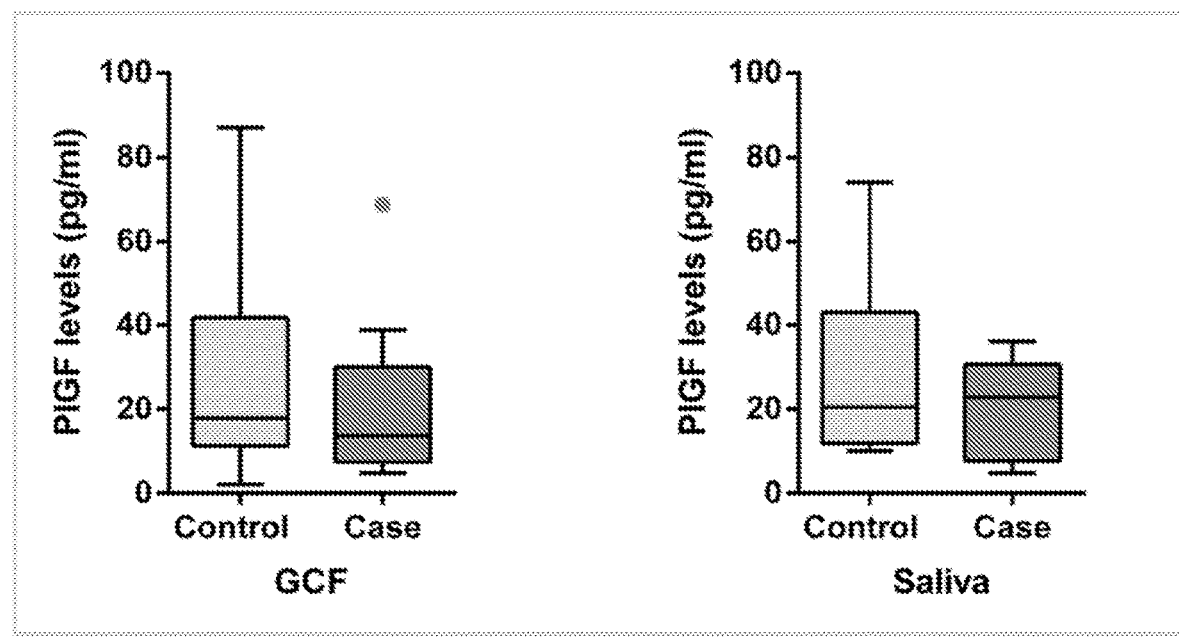
Figure 12:
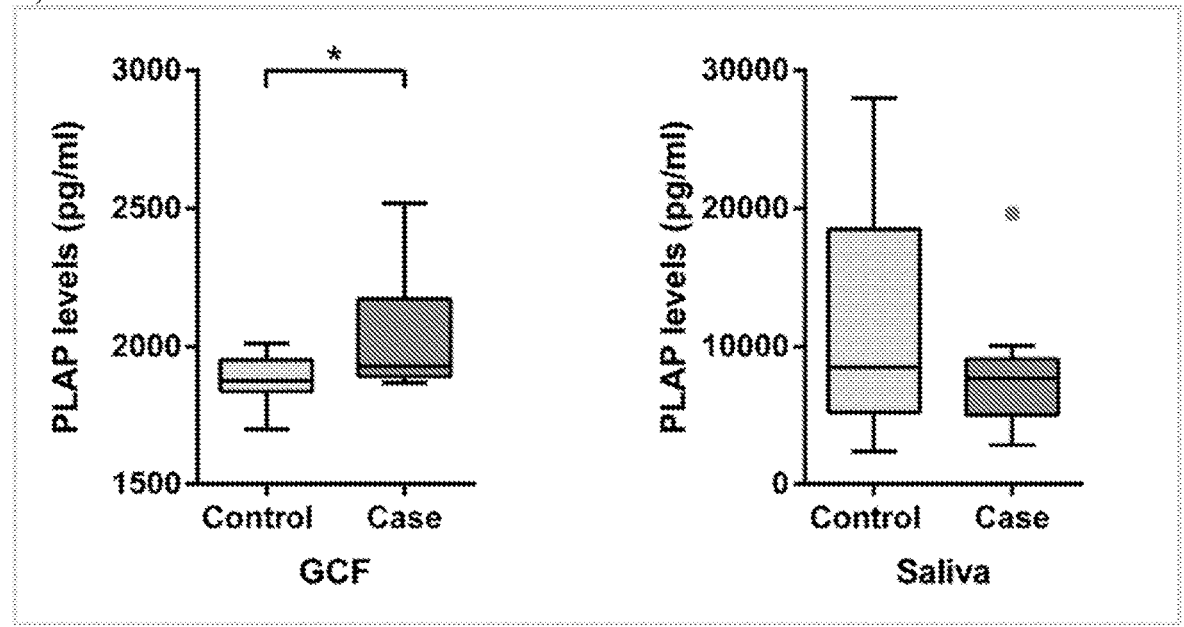

In particular, the present invention is based on the discovery that exosomes and micro-vesicles are confirmed to be significantly up-regulated in gingival crevicular fluid (GCF) samples of patients suffering from or having a pregnancy related disease, in particular suffering from or having gestational diabetes mellitus or preeclampsia. This is clearly illustrated in FIGS. 8 to 9, wherein the results clearly show higher concentration levels of exosomes and micro-vesicles in the GCF of patients who suffered from or had preeclampsia or gestational diabetes during the third trimester of their pregnancy (please note that the GCF samples were obtained taken during the first trimester of their pregnancy), in comparison to control GCF samples obtained from healthy individual pregnant women during the first trimester of their pregnancy who did not suffered or had preeclampsia or gestational diabetes during the third trimester of their pregnancy. In addition, the results show that not only the concentration of exosomes or micro-vesicles of less than or about 150 nm in GCF, were significantly increased in those patients who suffered from or had preeclampsia or gestational diabetes mellitus at the end of their pregnancy but also these individuals presented a significantly higher concentration of micro-vesicles greater than 200 nm (and preferably <500 nm) in GCF.

Consequently, a first embodiment of the invention refers to an in vitro method for screening for subjects at risk of developing a pregnancy related disease, in particular at risk of developing gestational diabetes mellitus or preeclampsia, comprising: (a) measuring the concentration level of at least exosomes and micro-vesicles obtained from a gingival crevicular fluid (GCF) sample of the subjects, preferably human subjects, to be screened; and (b) comparing said concentration level of the least exosomes and micro-vesicles of the human subjects to be screened with an already established expression pattern or with the concentration level of individuals not suffering from a pregnancy related disease, wherein an increased in the concentration levels of exosomes and micro-vesicles is indicative of a risk of developing a pregnancy related disease, in particular a risk of developing gestational diabetes mellitus or preeclampsia. Preferably, such determination can be made by measuring the concentration levels of either the total amount of exosomes and micro-vesicles present in the GCF sample or by measuring a biomarker present in the GCF sample selected from the list consisting of: exosomes or micro-vesicles of less than or equal to 150 nm, exosomes or micro-vesicles of less than or equal to 200 nm and micro-vesicles greater than 200 nm and preferably smaller than 500 nm.

A second embodiment of the invention refers to the in vitro method for screening subjects, according to the first embodiment of the invention, which further comprises measuring the expression pattern or level of at least PlGF, or of at least PLAP (placental alkaline phosphatase), or of at least PlGF and glycemia, or of at least PlGF and PLAP (placental alkaline phosphatase), or of at least PlGF and sFlt-1 (antiangiogenic factor sFlt-1), or of at least PlGF and PLAP and sFlt-1, or of at least PlGF and PLAP and glycemia, or of at least PlGF and sFlt-1 and glycemia, or of at least PlGF and PLAP and sFlt-1 and glycemia, wherein PlGF, PLAP and sFlt-1 from the GCF sample taken from the subject.

A third embodiment of the invention refers to an in vitro method for the diagnosis, preferably for the early diagnosis, of a subject suspected of having or suffer from a pregnancy related disease, in particular suspected of having or suffer from gestational diabetes mellitus or preeclampsia, comprising the steps a) and b) of any of the first or second embodiments of the invention, and optionally (c) confirming the presence of the pregnancy related disease with biophysical parameters and clinical information, i.e. gestational diabetes mellitus by means of an oral glucose tolerance test (OGTT), preeclampsia by means of quantification of proteinuria, uric acid and/or transaminases.

A fourth embodiment of the invention refers to a method for obtaining useful data for the in vitro diagnosis of a subject suspected of having or suffer from a pregnancy related disease, in particular suspected of having or suffer from gestational diabetes mellitus or preeclampsia, comprising the steps a) and b) of the first or second embodiments of the invention.

A fifth embodiment of the invention refers to an in vitro method for classifying human subjects as healthy subjects or as subjects suffering from a pregnancy related disease, in particular suspected of having or suffer from gestational diabetes mellitus or preeclampsia, comprising the steps a) and b) of the first or second embodiments of the invention.

A sixth embodiment of the invention refers to an in vitro method for monitoring the response to a therapy or for monitoring the progression of a pregnancy related disease, in particular of gestational diabetes mellitus or preeclampsia, in a subject having gestational diabetes mellitus comprising the steps a) and b) of the first or second embodiments of the invention.

A seventh embodiment of the invention refers to a method for treating human subjects diagnosed with a pregnancy related disease, in particular with gestational diabetes mellitus or preeclampsia, comprising the steps a) and b) of the first or second embodiments of the invention, and (c) treating the patient diagnosed with the pregnancy related disease, in particular with gestational diabetes mellitus or preeclampsia.

An eighth embodiment of the invention refers to the method, according to the seventh embodiment of the invention, wherein the patient is diagnosed with diabetes mellitus and is treated by an appropriate diabetic diet or food plan and/or by the administration of oral hypoglycemic drugs such as metformine.

An ninth embodiment of the invention refers to the method, according to the seventh embodiment of the invention, wherein the patient is diagnosed with preeclampsia and is treated by steroids to hasten fetal lungs, anticoagulant agents such as acetylsalicylic acid (aspirin) and/or inhibitors of hypoxic inducible factor 1α such as metformine.

A tenth embodiment of the invention refers to the in vitro use of a kit or device comprising biomarker detecting reagents capable of determining a concentration level of at least exosomes and micro-vesicles in a gingival crevicular fluid (GCF) sample obtained from a subject, preferably a human subject, for screening for subjects at risk of developing a pregnancy related disease, in particular at risk of developing gestational diabetes mellitus or preeclampsia, or for diagnosing subjects, in particular for the early diagnosis, with a pregnancy related disease, in particular with diabetes mellitus or preeclampsia.

The present invention also refers to an in vitro method for screening or identifying subjects at risk of suffering from or developing a pregnancy related disease, in particular at risk of suffering from or developing gestational diabetes mellitus or preeclampsia, based on measuring the expression profile or level of angiogenic peptide (PlGF) which is up-regulated or over-expressed in patients suffering from gestational diabetes mellitus and down-regulated in patients suffering from preeclampsia. In this sense, remarkably as shown in FIGS. 1, 2, 3 and 4 and Tables 3, 5 and 6, high levels of PlGF by itself in GCF or in combination with serum glycemia are significantly associated with the presence of gestational diabetes mellitus, wherein PlGF offers the best results in comparison to other biomarkers tested herein such as PLAP (placental alkaline phosphatase), or sFlt-1 (antiangiogenic factor sFlt-1). The same is true for preeclampsia, wherein as shown in FIG. 13, lower or down-regulated levels of PlGF by itself in GCF are significantly associated with the presence of preeclampsia.

Consequently, an eleventh embodiment of the invention refers to an in vitro method for screening for subjects at risk of suffering from or developing a pregnancy related disease, in particular at risk of suffering from or developing gestational diabetes mellitus or preeclampsia, comprising: (a) measuring the expression pattern or level of at least placental angiogenic peptide (PlGF) obtained from a gingival crevicular fluid (GCF) sample of the subjects, preferably human subjects, to be screened; and (b) comparing said expression pattern or level of at least PlGF of the human subjects to be screened with an already established expression pattern or level, wherein a differential expression of at least PlGF is indicative of a pregnancy related disease, in particular of diabetes mellitus in case of over-expression or preeclampsia in case of down-regulation.

A twelfth embodiment of the invention refers to an in vitro method for screening subjects, according to the eleventh embodiment of the invention, comprising: (a) measuring the expression pattern or level of at least PlGF and glycemia, or of at least PlGF and PLAP (placental alkaline phosphatase), or of at least PlGF and sFlt-1 (antiangiogenic factor sFlt-1), or of at least PlGF and PLAP and sFlt-1, or of at least PlGF and PLAP and glycemia, or of at least PlGF and sFlt-1 and glycemia, or of at least PlGF and PLAP and sFlt-1 and glycemia, wherein PlGF, PLAP and sFlt-1 are obtained from a GCF sample taken from the subject; and (b) comparing said expression pattern or level of at least PlGF and glycemia, or of at least PlGF and PLAP, or of at least PlGF and sFlt-1, or of at least PlGF and PLAP and sFlt-1, or of at least PlGF and PLAP and glycemia, or of at least PlGF and sFlt-1 and glycemia, or of at least PlGF and PLAP and sFlt-1 and glycemia, of the subjects to be screened with an already established expression pattern or level, wherein a differential expression level of at least PlGF and glycemia, or of at least PlGF and PLAP, or of at least PlGF and sFlt-1, or of at least PlGF and PLAP and sFlt-1, or of at least PlGF and PLAP and glycemia, or of at least PlGF and sFlt-1 and glycemia, or of at least PlGF and PLAP and sFlt-1 and glycemia, is indicative of a pregnancy related disease, in particular of diabetes mellitus in case of over-expression of any of the aforesaid biomarkes or combinations thereof or preeclampsia in case of down-regulation of PlGF and up-regulation or overexpression of the rest of the biomarkers above mentioned.

A thirteenth embodiment of the invention refers to an in vitro method for the diagnosis, in particular the early diagnosis, of a subject suspected of having or suffering from a pregnancy related disease, in particular from gestational diabetes mellitus or preeclampsia, comprising the steps a) and b) of any of the eleventh or twelfth embodiments of the invention, and optionally (c) confirming the presence of the pregnancy related disease with biophysical parameters and clinical information, i.e. gestational diabetes mellitus by means of an oral glucose tolerance test (OGTT), preeclampsia by means of quantification of proteinuria, uric acid or transaminases.

A fourteenth embodiment of the invention refers to a method for obtaining useful data for the in vitro diagnosis of a subject suspected of having or suffering from a pregnancy related disease, in particular from gestational diabetes mellitus or preeclampsia, comprising the steps a) and b) of the eleventh or twelfth embodiments of the invention.

A fifteenth embodiment of the invention refers to an in vitro method for classifying human subjects as healthy subjects or as subjects suspected of having or suffering from a pregnancy related disease, in particular from gestational diabetes mellitus or preeclampsia, comprising the steps a) and b) of the eleventh or twelfth embodiments of the invention.

A sixteenth embodiment of the invention refers to an in vitro method for monitoring the response to a therapy or for monitoring the progression of a pregnancy related disease, in particular of gestational diabetes mellitus or preeclampsia, in a subject comprising the steps a) and b) of the eleventh or twelfth embodiments of the invention.

A seventeenth embodiment of the invention refers to a method for treating human subjects suffering from a pregnancy related disease, in particular from gestational diabetes mellitus or preeclampsia, comprising the steps a) and b) of the eleventh or twelfth embodiments of the invention, and (c) treating the patient diagnosed with said pregnancy related disease, in particular with gestational diabetes mellitus or preeclampsia.

An eighteenth embodiment of the invention refers to the method, according to the seventeenth embodiment of the invention, wherein the patient is diagnosed with gestational diabetes mellitus and is treated by an appropriate diabetic diet or food plan and/or by the administration of oral hypoglycemic drugs such as metformine.

A nineteenth embodiment of the invention refers to the method, according to the seventeenth embodiment of the invention, wherein the patient is diagnosed with preeclampsia and is treated by steroids to hasten fetal lungs, anticoagulant agents such as acetylsalicylic acid (aspirin) and/or inhibitors of hypoxic inducible factor 1α such as metformine.

A twentieth embodiment of the invention refers to the use of a kit comprising biomarker detecting reagents capable of determining a differential expression level of at least PlGF in a GCF sample, for screening for subjects at risk of developing a pregnancy related disease, in particular at risk of developing gestational diabetes mellitus or preeclampsia, or for diagnosing subjects suffering from a pregnancy related disease, in particular from diabetes mellitus or preeclampsia.

A twenty-first embodiment of the invention refers to the use of the kit, according to the twentieth embodiment of the invention, comprising reagents for determining a differential expression level of at least PlGF and glycemia, or of at least PlGF and PLAP (placental alkaline phosphatase), or of at least PlGF and sFlt-1 (antiangiogenic factor sFlt-1), or of at least PlGF and PLAP and sFlt-1, or of at least PlGF and PLAP and glycemia, or of at least PlGF and sFlt-1 and glycemia, or of at least PlGF and PLAP and sFlt-1 and glycemia, wherein a differential expression of at least PlGF and glycemia, or of at least PlGF and PLAP (placental alkaline phosphatase), or of at least PlGF and sFlt-1 (antiangiogenic factor sFlt-1), or of at least PlGF and PLAP and sFlt-1, or of at least PlGF and PLAP and glycemia, or of at least PlGF and sFlt-1 and glycemia, or of at least PlGF and PLAP and sFlt-1 and glycemia, is indicative of a pregnancy related disease, in particular of diabetes mellitus or preeclampsia.

Figure 6:
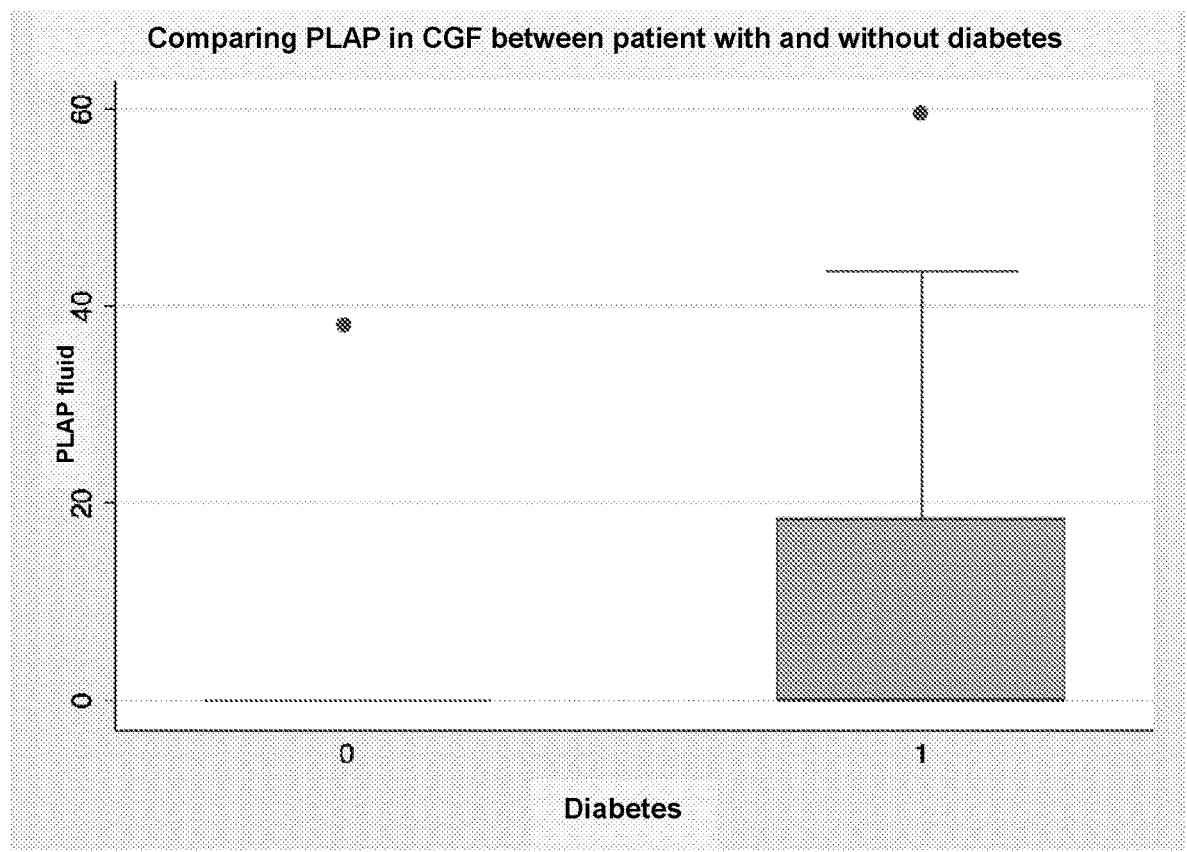
FIG. 6. Comparison of Maternal GCF PLAP concentrations between normal pregnancy (control group) and patients with gestational diabetes (case group). GCF-PLAP concentrations were significantly higher in patients with preeclampsia in comparison with healthy pregnancies.
Figure 7:
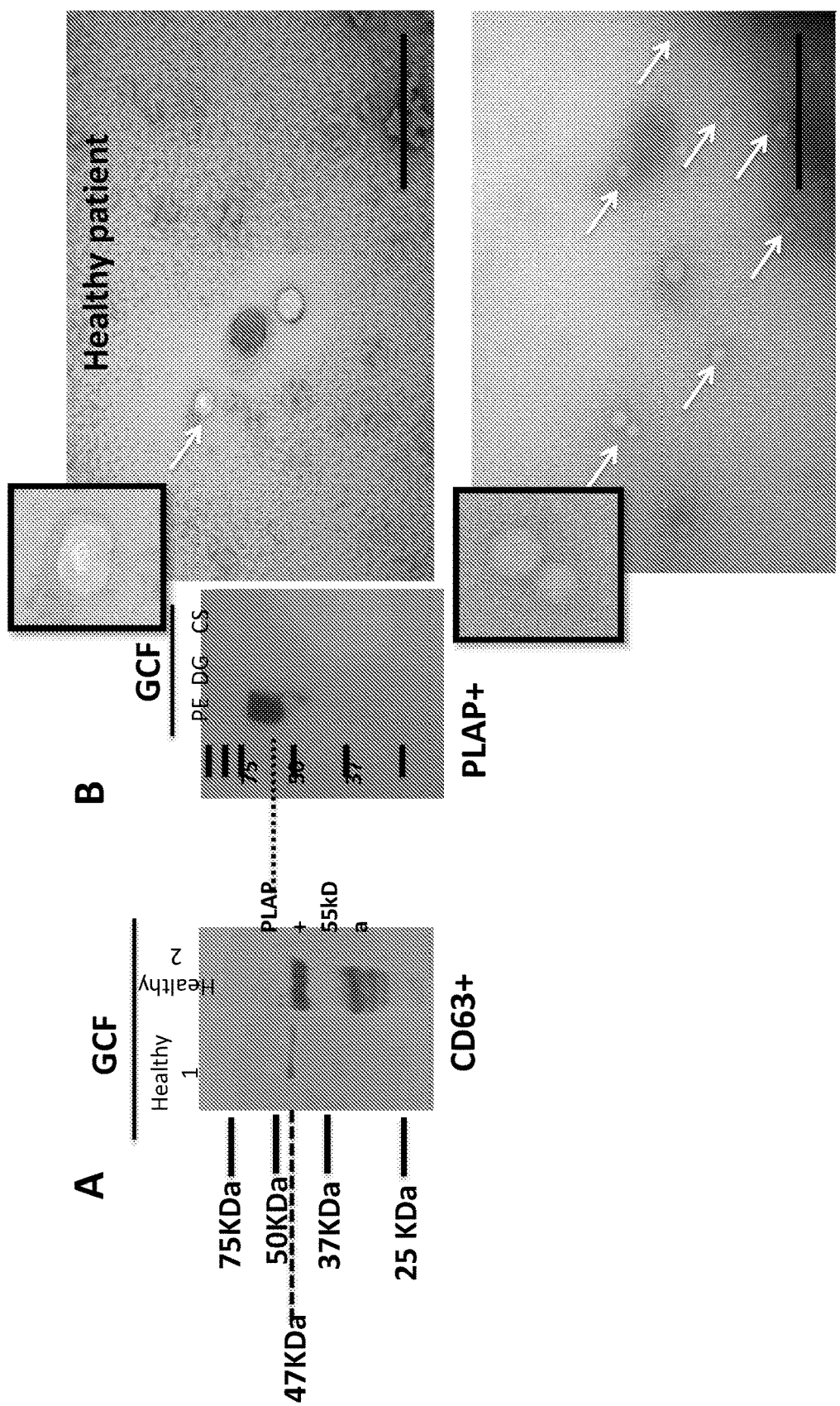
FIG. 7. Exosome Characterization of healthy and gestational diabetes gingival crevicular patients in gingival crevicular fluids samples at 11-14 gestation weeks. A) western Blot of CD63+ of exosome of healthy patients. B) western Blot of PLAP+. Electron microscopy of Healthy patient (up) and gestational diabetes patient (down).

Furthermore, the present invention also refers to an in vitro method for screening or identifying subjects at risk of suffering from or developing a pregnancy related disease, in particular at risk of suffering from or developing gestational diabetes mellitus or preeclampsia, based on measuring the expression profile or level of PLAP (placental alkaline phosphatase) which is up-regulated or over-expressed in the GCF of patients suffering from gestational diabetes mellitus or preeclampsia. In this sense, remarkably as shown in FIG. 6, high levels of PLAP by itself in GCF or in combination with other biomarkers are significantly associated with the presence of gestational diabetes mellitus. The same is true for preeclampsia, wherein as shown in FIG. 13, high levels of PLAP by itself in GCF are significantly associated with the presence of preeclampsia.

Consequently, a twenty-second embodiment of the invention refers to an in vitro method for screening for subjects at risk of suffering from or developing a pregnancy related disease, in particular at risk of suffering from or developing gestational diabetes mellitus or preeclampsia, comprising: (a) measuring the expression pattern or level of at least PLAP obtained from a gingival crevicular fluid (GCF) sample of the subjects, preferably human subjects, to be screened; and (b) comparing said expression pattern or level of at least PLAP of the human subjects to be screened with an already established expression pattern or level, wherein overexpression of at least PLAP is indicative of a pregnancy related disease, in particular of diabetes mellitus or preeclampsia.

A twenty-third embodiment of the invention refers to an in vitro method for screening subjects, according to the eleventh embodiment of the invention, comprising: (a) measuring the expression pattern or level of at least PlGF and PLAP (placental alkaline phosphatase), or of at least PLAP and sFlt-1 (antiangiogenic factor sFlt-1), or of at least PlGF and PLAP and sFlt-1, or of at least PlGF and PLAP and glycemia, or of at least PLAP and sFlt-1 and glycemia, or of at least PlGF and PLAP and sFlt-1 and glycemia, wherein PlGF, PLAP and sFlt-1 are obtained from a GCF sample taken from the subject; and (b) comparing said expression pattern or level of the subjects to be screened with an already established expression pattern or level, wherein a differential expression of any of the above mentioned combinations is indicative of a pregnancy related disease, in particular of diabetes mellitus or preeclampsia.

A twenty-fourth embodiment of the invention refers to an in vitro method for the diagnosis, in particular the early diagnosis, of a subject suspected of having or suffering from a pregnancy related disease, in particular from gestational diabetes mellitus or preeclampsia, comprising the steps a) and b) of any of the twenty-second or twenty-third embodiments of the invention, and optionally (c) confirming the presence of the pregnancy related disease with biophysical parameters and clinical information, i.e. gestational diabetes mellitus by means of an oral glucose tolerance test (OGTT), preeclampsia by means of quantification of proteinuria, uric acid or transaminases.

A twenty-fifth embodiment of the invention refers to a method for obtaining useful data for the in vitro diagnosis of a subject suspected of having or suffering from a pregnancy related disease, in particular from gestational diabetes mellitus or preeclampsia, comprising the steps a) and b) of the twenty-second or twenty-third embodiments of the invention.

A twenty-sixth embodiment of the invention refers to an in vitro method for classifying human subjects as healthy subjects or as subjects suspected of having or suffering from a pregnancy related disease, in particular from gestational diabetes mellitus or preeclampsia, comprising the steps a) and b) of the twenty-second or twenty-third embodiments of the invention.

A twenty-seventh embodiment of the invention refers to an in vitro method for monitoring the response to a therapy or for monitoring the progression of a pregnancy related disease, in particular of gestational diabetes mellitus or preeclampsia, in a subject comprising the steps a) and b) of the twenty-second or twenty-third embodiments of the invention.

A twenty-eighth embodiment of the invention refers to a method for treating human subjects suffering from a pregnancy related disease, in particular from gestational diabetes mellitus or preeclampsia, comprising the steps a) and b) of the twenty-second or twenty-third embodiments of the invention, and (c) treating the patient diagnosed with said pregnancy related disease, in particular with gestational diabetes mellitus or preeclampsia.

An twenty-ninth embodiment of the invention refers to the method, according to the twenty-eighth embodiment of the invention, wherein the patient is diagnosed with gestational diabetes mellitus and is treated by an appropriate diabetic diet or food plan and/or by the administration of oral hypoglycemic drugs such as metformine.

A thirtieth embodiment of the invention refers to the method, according to the twenty-eighth embodiment of the invention, wherein the patient is diagnosed with preeclampsia and is treated by steroids to hasten fetal lungs, anticoagulant agents such as acetylsalicylic acid (aspirin) and/or inhibitors of hypoxic inducible factor 1α such as metformine.

A thirty-first embodiment of the invention refers to the use of a kit comprising biomarker detecting reagents capable of determining a differential expression level of at least PLAP in a GCF sample, for screening for subjects at risk of developing a pregnancy related disease, in particular at risk of developing gestational diabetes mellitus or preeclampsia, or for diagnosing subjects suffering from a pregnancy related disease, in particular from diabetes mellitus or preeclampsia.

A thirty-second embodiment of the invention refers to the use of the kit, according to the twentieth embodiment of the invention, comprising reagents for determining a differential expression level of at least PlGF and PLAP (placental alkaline phosphatase), or of at least PLAP and sFlt-1 (antiangiogenic factor sFlt-1), or of at least PlGF and PLAP and sFlt-1, or of at least PlGF and PLAP and glycemia, or of at least PLAP and sFlt-1 and glycemia, or of at least PlGF and PLAP and sFlt-1 and glycemia, wherein overexpression of at least PLAP and sFlt-1 (antiangiogenic factor sFlt-1), or of at least PlGF and PLAP and sFlt-1, or of at least PlGF and PLAP and glycemia, or of at least PLAP and sFlt-1 and glycemia, or of at least PlGF and PLAP and sFlt-1 and glycemia, is indicative of a pregnancy related disease, in particular of diabetes mellitus or preeclampsia.

Lastly, it is important to note that the present invention also refers to an in vitro method for screening or identifying subjects at risk of suffering from or developing preeclampsia, based on measuring the expression profile or level of at least sFlt-1 (antiangiogenic factor sFlt-1) which is up-regulated or over-expressed in the GCF of patients suffering from preeclampsia. In this sense, remarkably as shown in example 2, high levels of sFlt-1 by itself in GCF or in combination with other biomarkers are significantly associated with the presence of preeclampsia. In this sense, a thirty-third embodiment of the invention refers to an in vitro method for screening for subjects at risk of suffering from or developing preeclampsia, comprising: (a) measuring the expression pattern or level of at least sFlt-1 obtained from a gingival crevicular fluid (GCF) sample of the subjects, preferably human subjects, to be screened; and (b) comparing said expression pattern or level of at least sFlt-1 of the human subjects to be screened with an already established expression pattern or level, wherein overexpression of at least sFlt-1 is indicative of a pregnancy related disease, in particular of diabetes mellitus or preeclampsia.

A thirty-fourth embodiment of the invention refers to the in vitro method for screening subjects, according to the thirty-third embodiment of the invention, which further comprises measuring the expression pattern or level of at least PLAP and sFlt-1, or of at least PlGF and sFlt-1, or of at least PlGF and PLAP and sFlt-1, or of at least PlGF and sFlt-1 and glycemia, or of at least PlGF and PLAP and sFlt-1 and glycemia, wherein PlGF, PLAP and sFlt-1 from the GCF sample taken from the subject.

A thirty-fifth embodiment of the invention refers to an in vitro method for the diagnosis, in particular the early diagnosis, of a subject suspected of having or suffering from preeclampsia, comprising the steps a) and b) of any of the thirty-third or thirty-fourth embodiments of the invention, and optionally (c) confirming the presence of the preeclampsia with biophysical parameters and clinical information, i.e. preeclampsia by means of quantification of proteinuria, uric acid or transaminases.

A thirty-sixth embodiment of the invention refers to a method for obtaining useful data for the in vitro diagnosis of a subject suspected of having or suffering from preeclampsia, comprising the steps a) and b) of the thirty-third or thirty-fourth embodiments of the invention.

A thirty-seventh embodiment of the invention refers to an in vitro method for classifying human subjects as healthy subjects or as subjects suspected of having or suffering from preeclampsia, comprising the steps a) and b) of the thirty-third or thirty-fourth embodiments of the invention.

A thirty-eighth embodiment of the invention refers to an in vitro method for monitoring the response to a therapy or for monitoring the progression of preeclampsia, in a subject comprising the steps a) and b) of the thirty-third or thirty-fourth embodiments of the invention.

A thirty-ninth embodiment of the invention refers to a method for treating human subjects suffering from preeclampsia, comprising the steps a) and b) of the thirty-third or thirty-fourth embodiments of the invention, and (c) treating the patient diagnosed with said preeclampsia, preferably by steroids to hasten fetal lungs, anticoagulant agents such as acetylsalicylic acid (aspirin) and/or inhibitors of hypoxic inducible factor 1α such as metformine.

A fortieth embodiment of the invention refers to the use of a kit comprising biomarker detecting reagents capable of determining a differential expression level of at least sFlt-1 in a GCF sample, for screening for subjects at risk of developing preeclampsia, or for diagnosing subjects suffering from preeclampsia.

A variety of statistical and mathematical methods for establishing the threshold or cutoff level of expression are known in the prior art. A threshold or cutoff expression level for a particular biomarker may be selected, for example, based on data from Receiver Operating Characteristic (ROC) plots, as described in the Examples and Figures of the present invention. One of skill in the art will appreciate that these threshold or cutoff expression levels can be varied, for example, by moving along the ROC plot for a particular biomarker or combinations thereof, to obtain different values for sensitivity or specificity thereby affecting overall assay performance. For example, if the objective is to have a robust diagnostic method from a clinical point of view, we should try to have a high sensitivity. However, if the goal is to have a cost-effective method we should try to get a high specificity. The best cutoff refers to the value obtained from the ROC plot for a particular biomarker that produces the best sensitivity and specificity. Sensitivity and specificity values are calculated over the range of thresholds (cutoffs). Thus, the threshold or cutoff values can be selected such that the sensitivity and/or specificity are at least about 70%, and can be, for example, at least 75%, at least 80%, at least 85%, at least 90%, at least 95%, at least 96%, at least 97%, at least 98%, at least 99% or at least 100% in at least 60% of the patient population assayed, or in at least 65%, 70%, 75% or 80% of the patient population assayed.

Consequently, each of the above cited embodiments of the present invention is preferably carried out by determining the expression or concentration levels of at least any of the biomarkers previously cited in a GCF sample, and optionally a serum sample (for determining glycemia) isolated from the subject to be diagnosed or screened, and comparing the expression or concentration levels of said biomarkers with a predetermined threshold or cutoff values or to an established expression or concentration pattern or level, wherein said predetermined threshold or cutoff values correspond to the concentration or expression level of said biomarkers which correlates with the highest specificity at a desired sensitivity in a ROC curve calculated based on the expression or concentration levels of the biomarkers determined in a patient population being at risk of suffering a pregnancy related disease, wherein the differential expression (overexpression or reduced expression depending on the biomarker) of at least one of said biomarkers, with respect to said predetermined cutoff value is indicative that the subject suffers from or has a pregnancy related disease with said desired sensitivity. In addition, each of the above cited embodiments of the present invention can also be preferably carried out by comparing the expression or concentration levels of said biomarkers isolated from the subject to be diagnosed or screened, with an established expression or concentration pattern or level of said biomarkers obtained from a healthy population, wherein the differential expression (overexpression or reduced expression depending on the biomarker) of at least one of said biomarkers, with respect to said established expression or concentration pattern or level is indicative that the subject suffers from or has a pregnancy related disease.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of groups, those skilled in the art will recognize that the invention is also thereby described in terms of any individual member or subgroup of members of the group.

EXAMPLES

Example 1

Gestational Diabetes Mellitus

Material and Methods

A case-control study was conducted. The selection criteria for the subjects were that they be pregnant women with a diagnosis of GDM. In total, 14 cases were recruited from the prenatal cohort of 80 women admitted to the Maternal-Fetal Unit at the Sotero del Rio Hospital in Santiago, Chile, between January and October 2015. The controls were the same cohort to generate a sample of 66 control pregnancies women. Both groups consisted of subjects with singleton gestation of equal socioeconomic level. Clinical enrolment and anthropometric data were collected at 11-14 week gestation, and a dental evaluation and full-mouth periodontal exams were then performed by one periodontics. All clinically relevant data for the study were stored in a computer database. Women were excluded if they had fewer than 18 teeth, had used systemic or topical anti-microbial/anti-inflammatory therapy for the previous 3 months. Written informed consent was obtained from the women who agreed to participate in the study, which was approved by the University of the Andes Ethics Committee.

The variables studied were GDM, age, body mass index (BMI), number of teeth, GCF-PLAP, PlGF, sFlt-1 and periodontal clinical measures and diagnoses.

Sample Collection and Assessment

Periodontal examination and collection of oral fluids samples were performed at the same gestational age in both groups. After the tooth was isolated with a cotton roll, supragingival plaque was removed with curettes (Hu Friedy, Gracey, Ill., USA) without touching the marginal gingiva. The gingival sulcus was then dried gently with an air syringe. GCF was collected with paper strips (Pro-Flow, Amityville, N.Y., USA). The strips were placed into the sulci/pocket until mild resistance was sensed and left in place for 30 seconds. Strips contaminated by saliva or blood was excluded from the study. After GCF collection, the strips were placed in Eppendorf vials containing 100 µl of phosphate-buffered saline (PBS) with 0.05% Tween-20 (PBS-T). GCF was extracted by centrifugation at 10,000 g for 5 min (Hermle Labortech Nik. Z-233 MK-2). The elution procedure was repeated twice, GCF samples were obtained from 4 periodontal pockets (1×quadrant) at the most affected periodontal site. Additionally, 4-6 ml of saliva were collected into 10-ml Falcon™ tubes. Both samples were placed in liquid nitrogen after collection, and stored until further analysis.

ELISA Assays

PLAP, PlGF and sFlt-1 concentrations in GCF and saliva samples were quantified using commercially-available ELISAs according to manufactures instructions (PLAP, Human PLAP Elisa Kit, MyBioSource®, Catalogue Number MBS70199584, 2,000 pg/ml detection range; Human PlGF Quantikine Elisa Kit, R & D Systems, Catalogue Number DPG00, 15.6-1,000 pg/ml range detection; and VEFR/Flt-1 Quantikine Elisa Kit, R & D Systems, Catalogue Number DVR100B, 31.2-2,000 pg/ml range detection). The Elisa plates were read at a wavelength of 450 nm in an automatic ELISA plate reader (Microplate Reader, ELx808, Biotek Instruments, Winooski, Vt., USA). The concentrations of sFlt-1, PlGF and PLAP in maternal oral fluids samples were determined by interpolation from the standard curve. The laboratory personnel performing the assays were blinded to the clinical information.

Statistical Analyses

The normality of the data was tested using the Shapiro-Wilcox test. Because maternal GCF and saliva concentrations of PlGF, sFLT-1 and PLAP, were not normally distributed, non-parametric tests were used for the analyses. Comparisons between proportions were performed with Chi-square or Fisher's exact test, and Mann-Whitney U test was used for comparisons of continuous variables. The association strength was assessed using a multiple logistic regression model adjusted by BMI, periodontal diagnosis and tobacco use. The crude and adjusted odds ratio (OR) was determined and the statistical analysis was performed using STATA software (version 11; StataCorp, Lakeway Drive College Station, Tex., USA).

Results

The demographic and clinical characteristics of the case and control groups are presented in Table 1. All samples were taken between 11-14 weeks of gestation by the same dentist. The median number of teeth present was the same in both groups (27). All the periodontal clinical measures in both groups are presented in Table 2.

The mean values observed of PLAP levels in GCF for women that developed GDM was 12.2 pg/mL compared with 4.7 pg/ml in the healthy pregnancies. PlGF levels were 1 pg/ml in healthy patients and 5.3 pg/ml in the case group.

Figure 2:
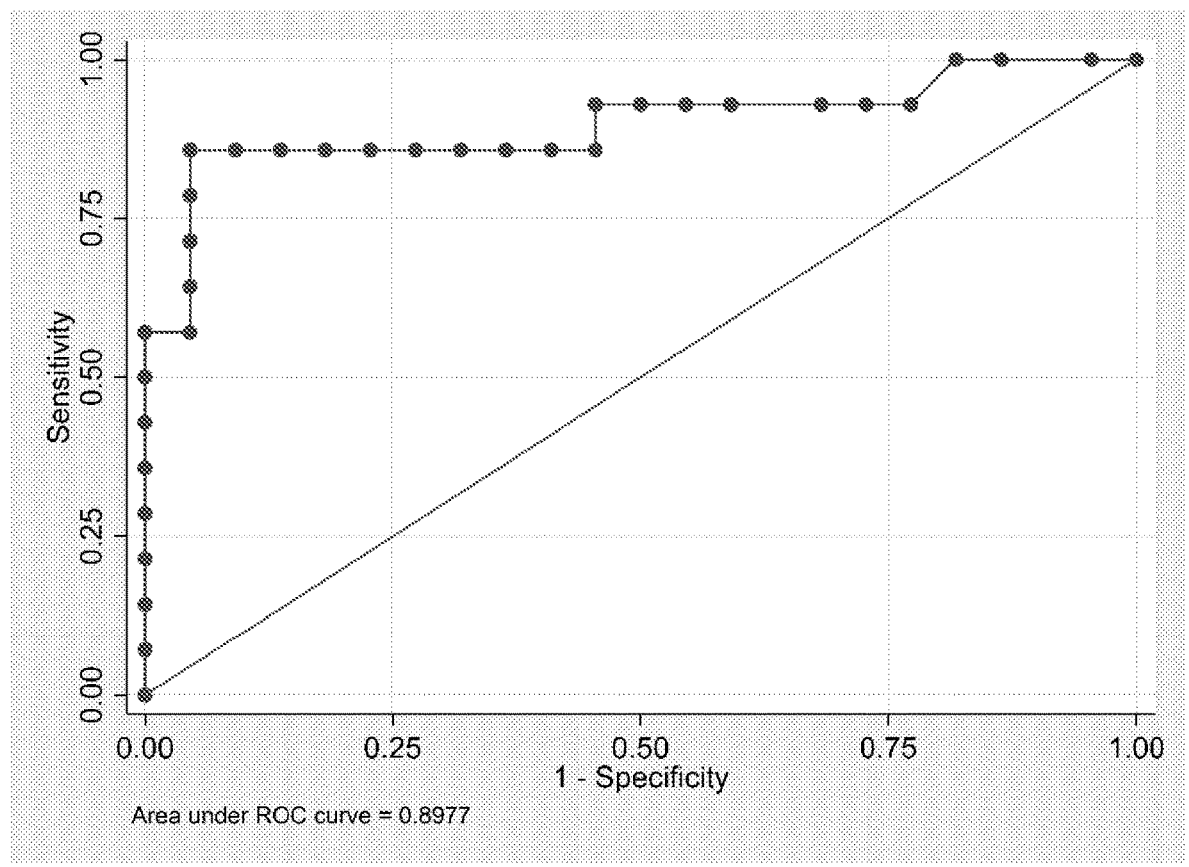
FIG. 2. Receiver Operating Characteristic curve of glycemia and PlGF (gingival crevicular fluid) versus gestational diabetes status.
Figure 3:
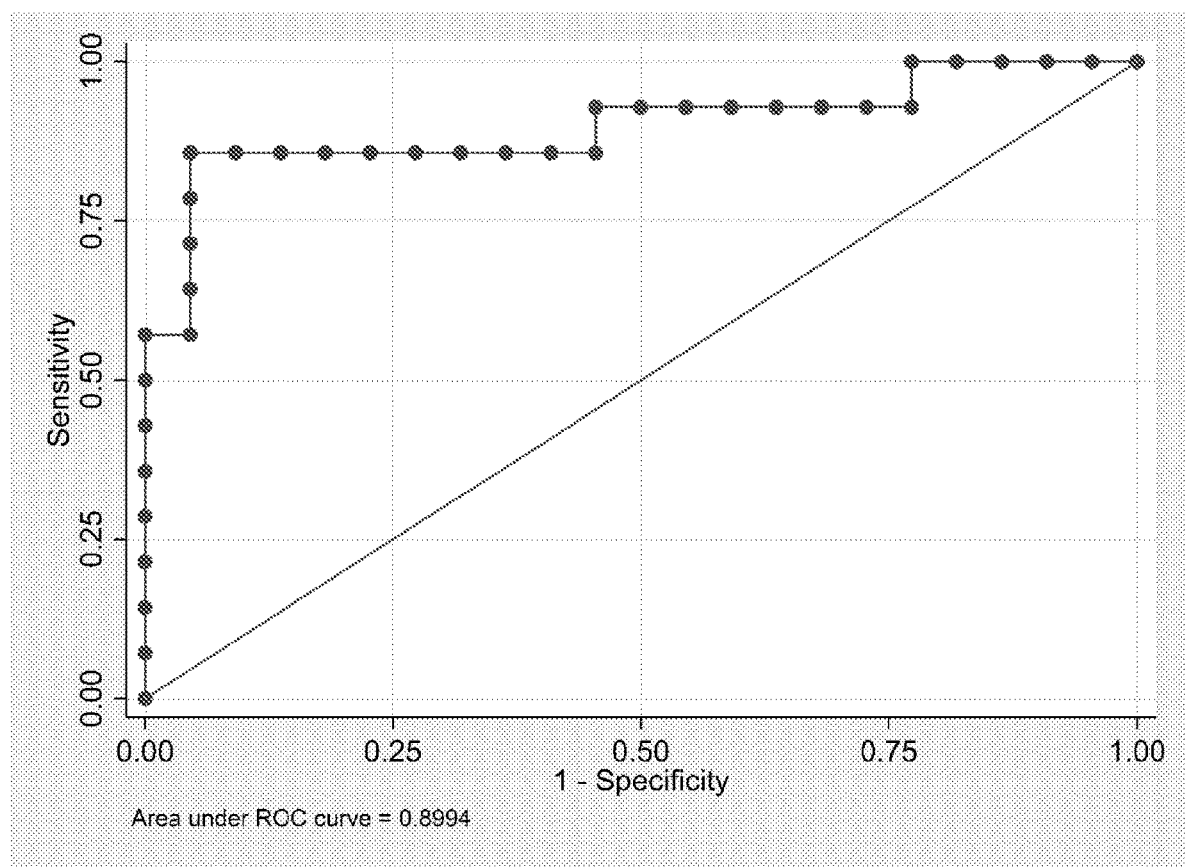
FIG. 3. Receiver Operating Characteristic curve of glycemia, PlGF (gingival crevicular fluid) and BMI versus gestational diabetes status.
Figure 4:
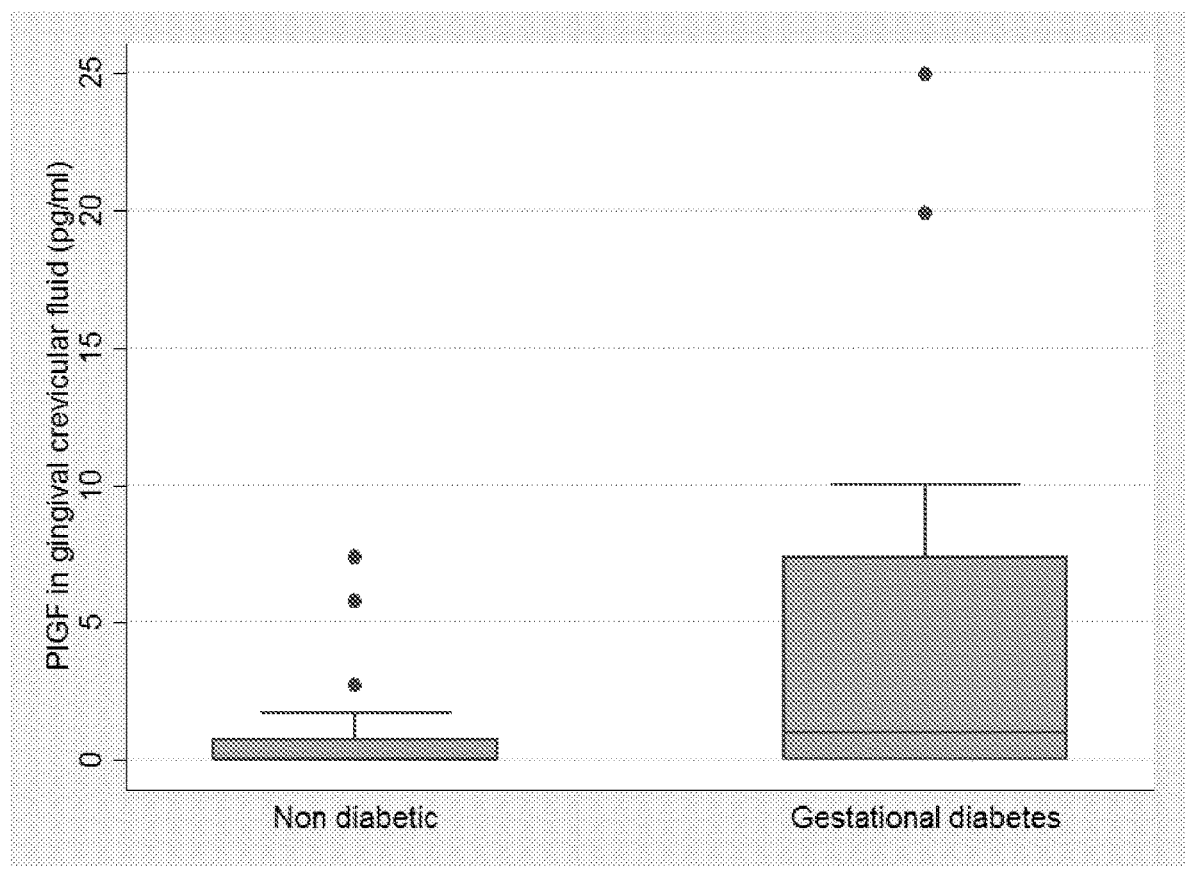
FIG. 4. PlGF in gingival crevicular fluid (pg/ml) in non-diabetic vs gestational diabetic patients.

Interestingly, as reflected in table 4 the PlGF value obtained from Gingival crevicular fluid (pg/ml) was statistically significant, the same is true for glycemia. Moreover, as shown in FIG. 2 the area de ROC curve for glycemia was 0.8214, wherein this area was significant increased when glycemia was combined with the PlGF value obtained from GCF fluid.

Example 2

Preeclampsia

Material and Methods
Study Design

A case-control study was conducted, including patients with PE (n=10) admitted to the Maternal-Fetal Unit at the Sotero del Rio Hospital in Santiago, Chile. Women with a normal pregnancy were randomly selected to generate the control group (n=20) and related for age and socioeconomic status. Women with any associated medical disorders (such as pre-existing hypertension, renal disease, anemia, or diabetesmellitus) were excluded. Women were also excluded if they had fewer than 18 teeth, had used systemic or topical anti-microbial/anti-inflammatory therapy for the previous 3 months, or had a history of previous periodontal treatment. A dental evaluation and full mouth periodontal exams were performed by one periodontist. The study and collection of saliva and GCF for clinical and research purposes have been approved by the Ethics Committee of both the Universidad de los Andes and the Sotero del Rio Hospital. All patients provided written informed consent at the time of enrollment, prior to the collection of the samples.
Definitions Preeclampsia was diagnosed in the presence of systolic blood pressure>140 mmHg and/or the diastolic blood pressure>90 mm on at least two occasions 4 h apart developing after 20 weeks of gestation in previously normotensive women, and there should be proteinuria (>300 mg in 24 h or two readings of at >2+ on dipstick analysis of midstream or catheter urine specimens if no 24-h collection is available). In the absence of proteinuria, new onset of any of the following systemic findings includes (a) thrombocytopaenia (platelet counts <100 000 μL), (b) renal insufficiency (creatinine>1.1 mg/dL or twofold increase in creatinine in the absence of underlying renal disease), (c) abnormal liver function (i.e., hepatic transaminase levels twice normal), and (d) pulmonary o edema; or cerebral or visual symptoms. According to American College of Obstetricians and Gynecologists (ACOG practice bulletin. Diagnosis and management of preeclampsia and eclampsia)30 and the National High Blood Pressure Education Program (Report of the National High Blood Pressure Education Program Working Group on High Blood Pressure in Pregnancy), 31 the control group was defined as normotensive women with singleton pregnancies without chronic medical conditions or obstetric complications.

Women were diagnosed with periodontitis if four or more teeth showed one or more sites with a probing pocket depth of 4 mm or higher, as well as if they had a clinical attachment loss of 3 mm or higher at the same site, inflammation, and bleeding on probing (BOP). Women who showed BOP at more than 20% of the sites and gingival redness, but did not have clinical attachment loss, were diagnosed as having gingivitis.
Sample Collection and Assessment Periodontal examination and collection of oral fluids samples were performed at the same gestational age in both groups. After the tooth was isolated with a cotton roll, supragingival plaque was removed with curettes (Hu Friedy, Gracey, Ill., USA) without touching the marginal gingiva. The gingival sulcus was then dried gently with an air syringe. GCF was collected with paper strips (Pro-Flow, Amityville, N.Y., USA). The strips were placed into the sulci/pocket until mild resistance was sensed and left in place for 30 s. Strips contaminated by saliva or blood was excluded from the study. After GCF collection, the strips were placed in Eppendorf vials containing 100 μL of phosphate-buffered saline (PBS) with 0.05% Tween-20 (PBS-T). GCF was extracted by centrifugation at 10 000 g for 5 min (Hermle Labortech Nik. Z-233 MK-2). The elution procedure was repeated twice; GCF samples were obtained from four periodontal pockets (1×quadrant) at the most affected periodontal site. Additionally, 4 to 6 mL of saliva were collected into 10-mL Falcon™ tubes. Both samples were placed in liquid nitrogen after collection and stored until further analysis.
Saliva and GCF Ultracentrifugation Saliva and GCF samples were centrifuged at 1500 g 1 for 0 min at 4° C. The supernatant was then removed, placed in another tube, and centrifuged at 17 000 g for 15 min at 4° C. Following the initial centrifugation steps, the supernatant was transferred to sterile tubes for ultracentrifugation at 160 000 g for 1 h at 4° C. Following ultracentrifugation, the aqueous layer was removed and the pellet containing EVs was washed with PBS and ultracentrifugated again at 160 000 g for 1 h at 4° C. The supernatant was removed, and the pellet was ready for the ELISA assays of CD63+.
ELISA Assays CD63+ EVs quantify, and PLAP, PlGF, and sFlt-1 concentrations in GCF and saliva samples were quantified using commercially available ELISAs according to manufactures instructions (CD63 exoElisa System Biosciences® catalog#EXOEL-CD63A-1, PLAP, Human PLAP Elisa Kit, MyBioSource®, Catalogue Number MBS70199584, 2000 pg/mL detection range; Human PlGF Quantikine Elisa Kit, R & D Systems, Catalogue Number DPG00, 15.6-1000 pg/mL range detection; and VEFR/Flt-1 Quantikine Elisa Kit, R & D Systems, Catalogue Number DVR100B, 31.2-2000 pg/mL range detection). CD63+ ExoElisa System Biosciences® was used to quantify EVs, and the results were presented in number of EVs. The ELISA plates were read at a wavelength of 450 nm in an automatic ELISA plate reader (Microplate Reader, ELx808, Biotek Instruments, Winooski, Vt., USA). The concentrations of sFlt-1, PlGF, PLAP, and CD63+ EVs in maternal oral fluids samples were determined by interpolation from the standard curve. The laboratory personnel performing the assays were blinded to the clinical information.
Real-Time PCR Total RNA from GCF was isolated using the miRNeasy Mini Kit, according to the instructions from the manufacturer (Qiagen, Valencia, Calif., USA). Total RNA was then quantified by spectroscopy (Nanodrop 1000, Thermo Scientific, Wilmington, Del., USA) and the quality assessed using the ratio of absorbance at 260 and 280 nm. Eighty nanograms of total RNA were treated with DNase I and reverse transcribed by using ImProm-II Reverse Transcription System (Promega, Madison, USA). Quantitative real-time PCR assays were performing in the Stratagene Mx3000P system (Agilent Technologies, Santa Clara, USA). The following gene specific primers were used for hPL: forward 5'GCGATGACTATCACCTCCTAAAG3' and reverse 5' CATGGTTGTGCGAGTTTGTG3'. The gene 36B4 (acidic ribosomal phosphoprotein) was used as a housekeeping gene. The PCR products were visualized in a 2% agarose gel with their respective negative controls.

Statistical Analyses

The normality of the data was tested using the Shapiro-Wilcox test. Because maternal GCF and saliva concentrations of PlGF, sFLT-1, and PLAP, as well as CD63+ EVs quantify, were not normally distributed, non-parametric tests were used for the analyses. Comparisons between proportions were performed with chi-square or Fisher's exact test, and Mann-Whitney Utest was used for comparisons of continuous variables. The association strength was assessed using a multiple logistic regression model adjusted by body mass index (BMI), periodontal diagnosis, and tobacco use. The crude and adjusted odds ratio was determined, and the statistical analysis was performed using STATA software (version 11; StataCorp, Lakeway Drive College Station, Tex., USA).

Results

The demographic and clinical characteristics of the case and control groups are presented in Table 7. No significant differences in the maternal median age and BMI between the groups were identified. All samples were taken over a range of time not exceeding 24 h once diagnosed PE (median of 33+/−1 weeks of gestation). Also, control group was equaled for gestational age for the samples procedure (median of 31+/−3 weeks of gestation). The median number of teeth present was 26 in the PE group and 27.5 in the controls. The mean probing depth was similar in both groups. The percentage of sites exhibiting BOP observed was 55.1% in PE and 37.3% in the control group, but this difference was not statistically significant. The levels of sites with plaque were also similar between groups (data not shown). Additionally, chronic periodontitis was found in 50% (5/10) patients with PE, and the remaining patients were diagnosed with gingivitis. In the control group, 40% of the patients were diagnosed with chronic periodontitis and 60% were diagnosed with gingivitis.

Previous maternal smoking history was positive in 30% of PE group and 35% of control group. An association between PE and GCF levels of PLAP (p value=0.0499), and sFlt-1 (p value=0.033) was observed, but not in PlGF and Cd63+ EVs (p value=0.358, p value=0.595, respectively) adjusted by previous tobacco useBMI, and periodontal diagnosis. In saliva samples, there was observed an association between sFlt-1 levels with the PE diagnosis (p value=0.045).

Figure 5:
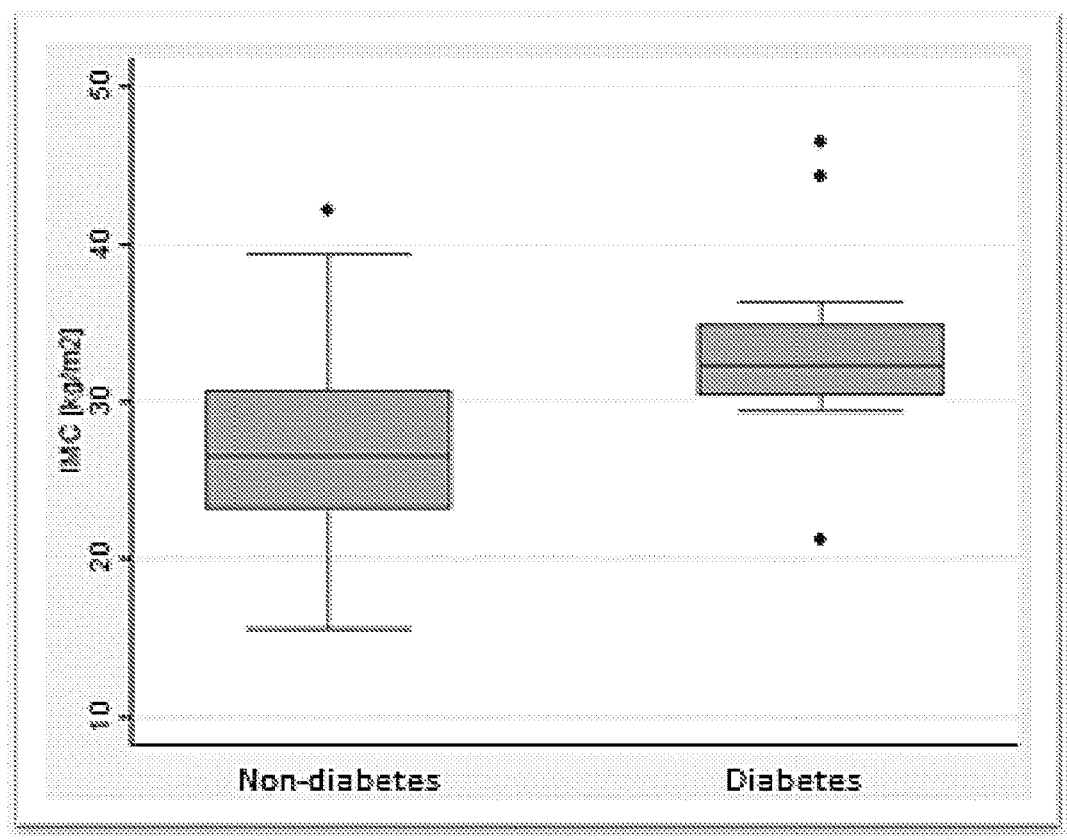
FIG. 5. A.—First trimester Body mass index in control group in comparison with women who will develops gestational diabetes. (27.5 v/s 30.4 p-value=0.0022). B.—First trimester blood glycemia levels in control group in comparison with women who will develops gestational diabetes. (p-value=0.0018). C.—First trimester blood pressure diastolic levels in control group in comparison with women who will develops gestational diabetes. (p-value=0.018). D.—Clinical attachment level at 11-14 weeks gestation in healthy and women who will develops gestational diabetes (p-value=0.918.) E.—mean Probing pocket depth measures at 11-14 weeks gestation in healthy and women who will develops gestational diabetes (p-value=0.570) F.—Mean of bleeding on probing (%) at 11-14 weeks gestation in healthy and women who will develops gestational diabetes (p-value=0.160) G.—Mean of periodontal surface inflamed area (PISA) at 11-14 weeks gestation in healthy and women who will develops gestational diabetes p-value=0.294
Figure 5:
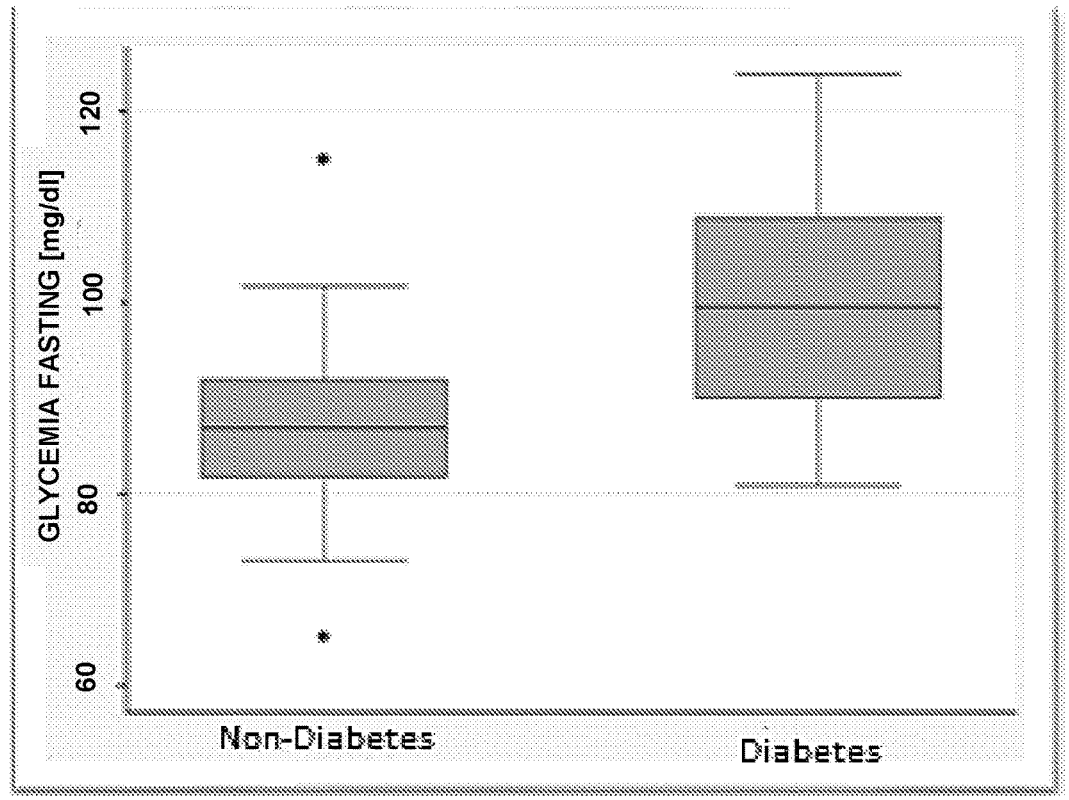
Figure 5:
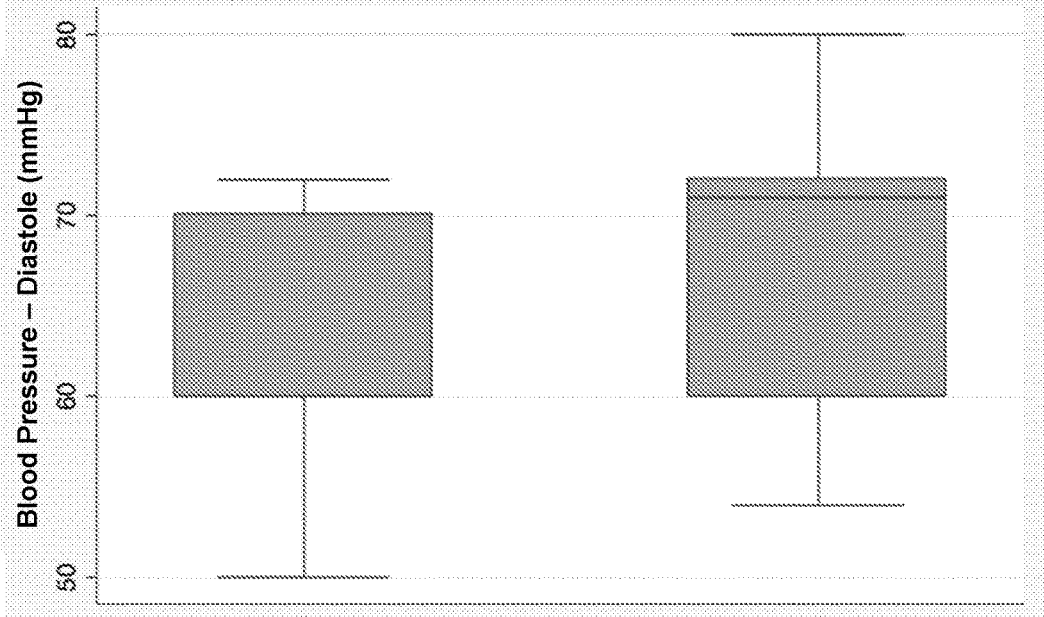
Figure 5:
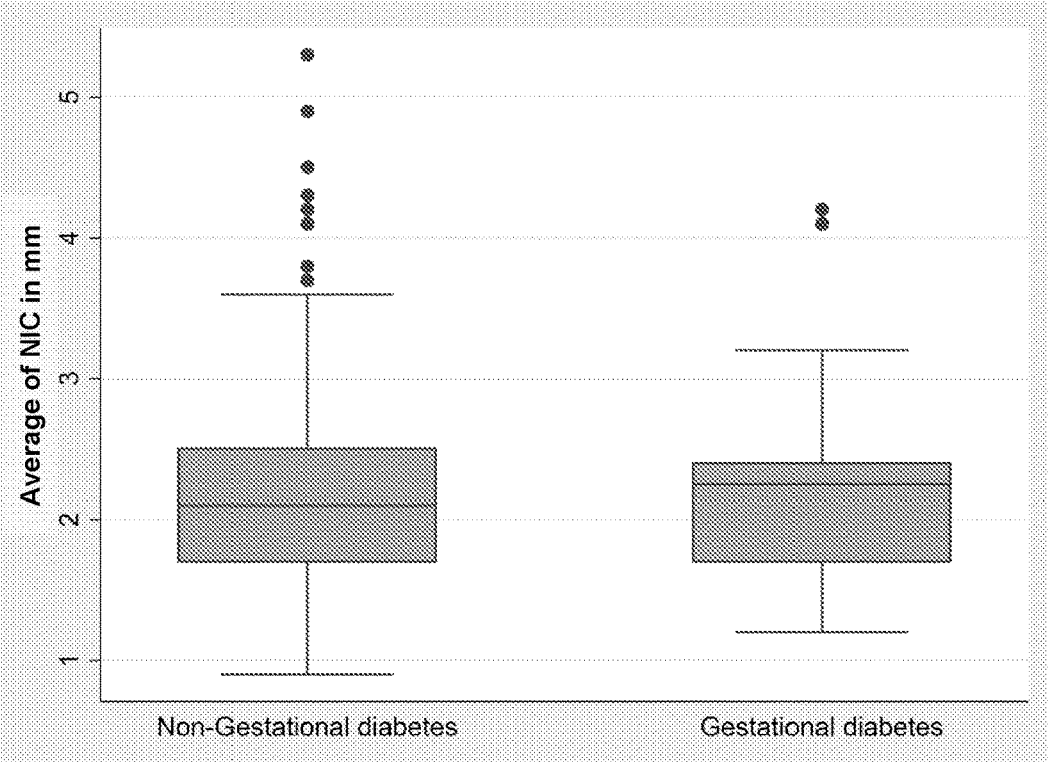
Figure 5:
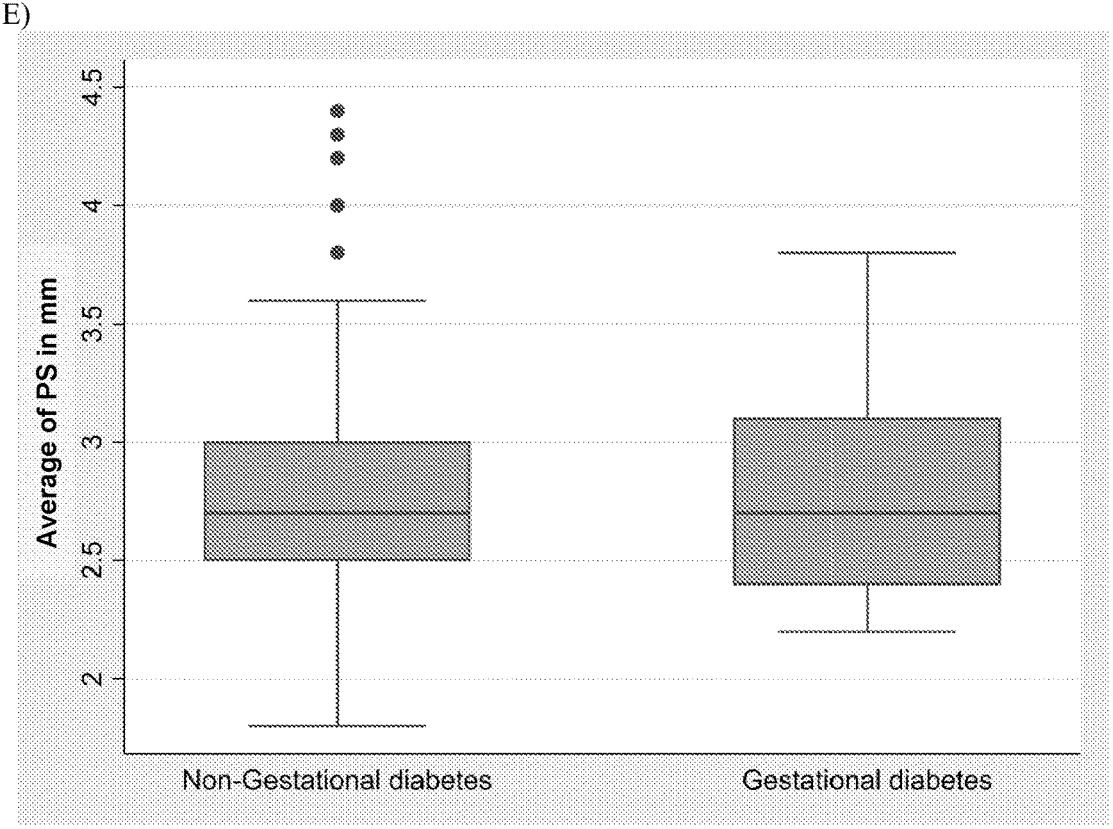
Figure 5:
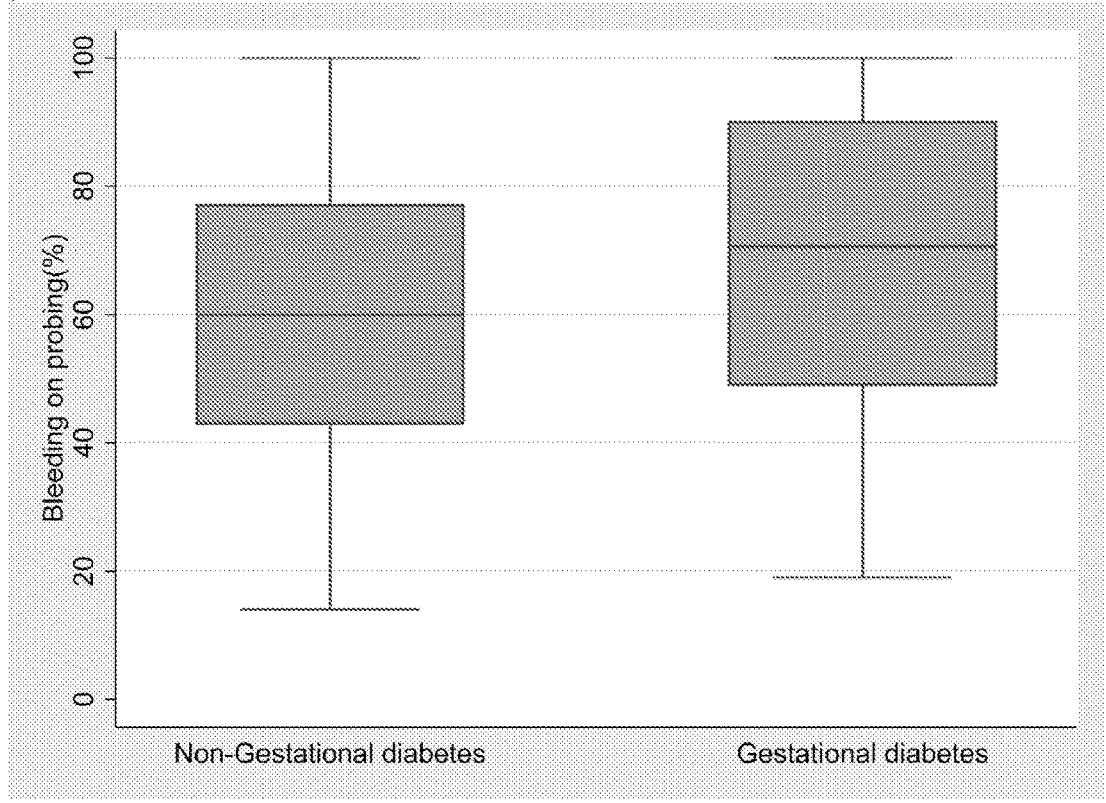
Figure 5:
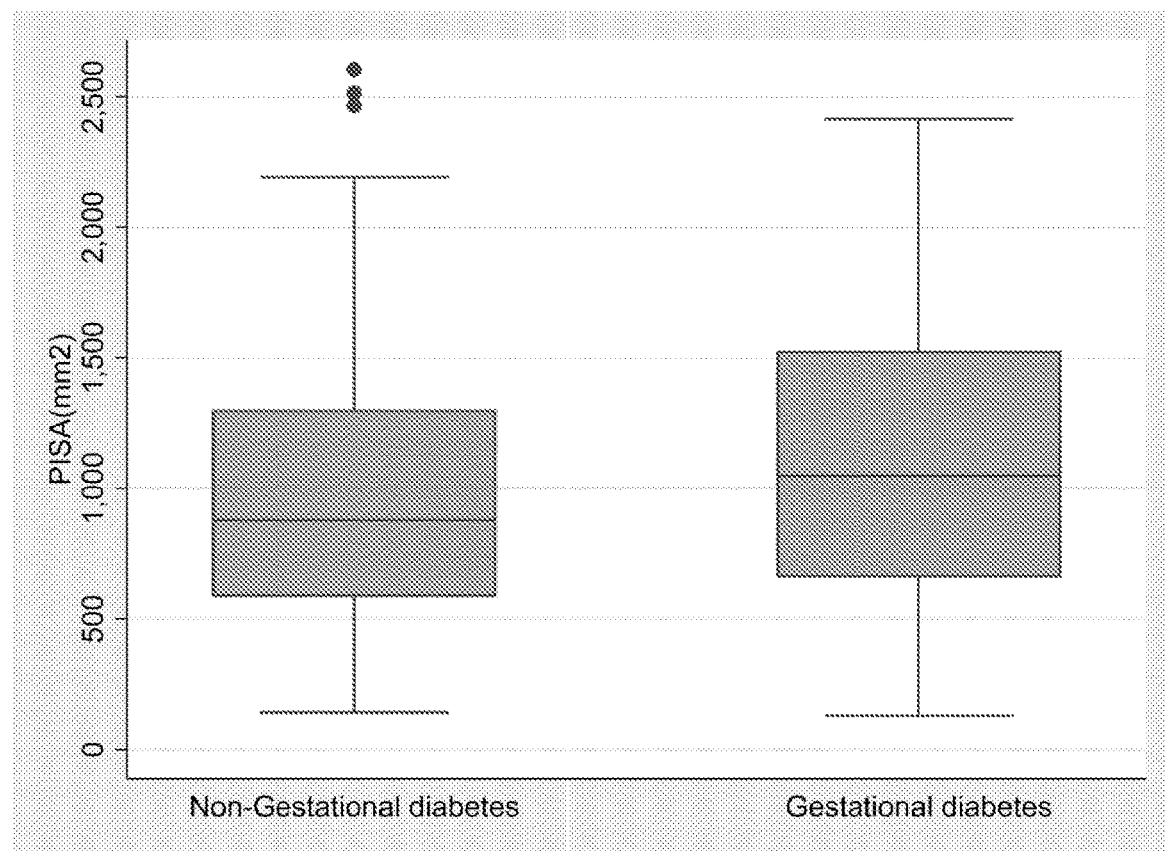

The multiple logistic regression analysis suggests that increased levels of PLAP and sFlt-1 in GCF (O.R=1.01; and O.R=1.10, respectively) are associated with PE in pregnant patients adjusted by tobacco use, BMI, and periodontal diagnosis (Table 8). sFlt-1, PlGF, CD63+ EV, and PLAP concentrations in both saliva and GCF are showed from FIGS. 15 forward, respectively. In addition, the PLAP/CD63+ EVs ratio in GCF of women with patients with PE was significantly higher than that of those with a normal pregnancy (p value=0.0008) (FIG. 5). To prove the presence of components of a specific placental origin in GCF, mRNA of hPL was measured. The transcript of hPL was detected in GCF. Interestingly, the mRNA of hPL was detected in GCF from the control group (n=4), but not in GCF from patients with PE (n=5).

In conclusion, this is the first study reporting the identification and changes in the concentrations of PLAP, PlGF and sFlt-1 in maternal oral fluids (GCF and saliva) during pregnancy and showing that these molecules are significantly elevated or reduced in PE compared with normal pregnancy.

TABLE 1

Clinical variables description by diabetic status.

| | Non diabetic pregnant individuals (n = 22) | | | Diabetic pregnant individuals (n = 14) | | |
|---|---|---|---|---|---|---|
| Variables | Mean (sd) | Median (IQR) | Range | Mean (sd) | Median (IQR) | Range |
| Age (years) | 23.1 (4.2) | 22 (5) | 17-35 | 5 (17) | 35 (26.5) | 6.1-25 |
| Weight (kgs) | 70.8 (20.3) | 67.5 (32.5) | 36.3-122 | 32.5 (36.3) | 122 (80.1) | 14.4-78 |
| Height (meters) | 1.6 (0.1) | 1.6 (0.1) | 1.5-1.8 | 0.1 (1.5) | 1.8 (1.6) | 0.1-1.6 |
| BMI (kg/m2) | 27.8 (6.8) | 26.8 (11.6) | 15.5-39.4 | 11.6 (15.5) | 39.4 (33.2) | 6.2-32.2 |
| Systolic blood pressure | 104.3 (8.9) | 100 (10) | 90-124 | 10 (90) | 124 (109.9) | 9-110 |
| Dyastolic blood pressure | 64 (6.7) | 60 (10) | 50-80 | 10 (50) | 80 (69.4) | 8.2-71 |
| Glycemia | 86.3 (8.2) | 85 (13) | 73-102 | 13 (73) | 102 (100.2) | 13.2-99.5 |

TABLE 2

Periodontal variables description by diabetic status.

| | Non diabetic pregnant individuals (n = 22) | | | Diabetic pregnant individuals (n = 14) | | |
|---|---|---|---|---|---|---|
| Variables | Mean (sd) | Median (IQR) | Range | Mean (sd) | Median (IQR) | Range |
| Index plaque (%) | 63.1 (25.1) | 72 (45) | 19-96 | 45 (19) | 96 (68.7) | 29.6-71 |
| Bleeding on probing (%) | 55.9 (25.2) | 47.5 (42) | 20-97 | 42 (20) | 97 (65.7) | 28.4-63 |
| Periodontal probing depth >=4 mm (%) | 13.5 (13.3) | 8.9 (19.6) | 0-50 | 19.6 (0) | 50 (17.5) | 15.9-9.6 |
| Periodontal probing depth (mean) | 2.5 (0.5) | 2.5 (0.6) | 1.8-3.8 | 0.6 (1.8) | 3.8 (2.7) | 0.5-2.6 |
| Clinical attachment level (mean) | 1.8 (0.7) | 1.8 (0.7) | 0.9-3.3 | 0.7 (0.9) | 3.3 (2.1) | 0.8-2 |
| Periodontal inflammed surface area (mm2) | 778.5 (477) | 661.3 (772.4) | 153.3-1729.1 | 772.4 (153.3) | 1729.1 (1068.9) | 653.3-904.5 |
| Number of teeth | | 27 (3) | 22-28 | | 27 (1) | 21-29 |

TABLE 3

Angiogenic and placental biomarkers level in oral fluids (Gingival crevicular fluid or saliva) by diabetic status.

| | Non diabetic pregnant individuals (n = 22) | | | Diabetic pregnant individuals (n = 14) | | |
|---|---|---|---|---|---|---|
| Variables | Mean (sd) | Median (IQR) | Range | Mean (sd) | Median (IQR) | Range |
| PlGF/Gingival crevicular fluid (pg/ml) | 1 (2) | 0 (0.8) | 0-7.4 | 5.3 (8) | 1 (7.4) | 0-25 |
| PlGF/Saliva(pg/ml) | 18 (20.7) | 10 (27.8) | 0-62.8 | 45.4 (135.9) | 4.5 (14.3) | 0-515.9 |
| sFlt/Gingival crevicular fluid (pg/ml) | 71.9 (565) | 65.5 (100.1) | 0-175.9 | 77.1 (83.3) | 63.7 (59.8) | 0-332.7 |
| sFlt/Saliva(pg/ml) | 268.2 (158.1) | 215.4 (234.1) | 54.1-684.3 | 236.2 (85.2) | 206 (100.1) | 137.6-465.3 |
| PLAP/Gingival crevicular fluid (pg/ml) | 4.7 (12.5) | 0 (0) | 0-46.2 | 12.2 (20.5) | 0 (18.2) | 0-59.3 |
| PLAP/Saliva (pg/ml) | 1003 (663.6) | 852.7 (1147.7) | 187.3-2460.8 | 1123.3 (613.2) | 1134.7 (913) | 165.9-2049.5 |

TABLE 4

Association between angiogenic and placental biomarkers, and glycemia levels in oral fluids (Gingival crevicular fluid or saliva) with diabetic status. Simple logistic regression (unadjusted).

| Variables | Odds ratio | p-value | CI 95% |
|---|---|---|---|
| PlGF/Gingival crevicular fluid (pg/ml) | 1.2471 | 0.077 | 0.9766-1.5924 |
| PlGF/Saliva(pg/ml) | 1.0043 | 0.416 | 0.994-1.0146 |
| sFlt/Gingival crevicular fluid (pg/ml) | 1.0012 | 0.819 | 0.9912-1.0113 |
| sFlt/Saliva(pg/ml) | 0.9981 | 0.483 | 0.9927-1.0035 |
| PLAP/Gingival crevicular fluid (pg/ml) | 1.0297 | 0.189 | 0.9857-1.0757 |
| PLAP/Saliva (pg/ml) | 1.0003 | 0.577 | 0.9992-1.0014 |
| Glycemia | 1.1338 | 0.005 | 1.0389-1.2372 |

TABLE 5

Association between glycemia and PlGF in gingival crevicular fluid with diabetic status. Multiple logistic regression (adjusted).

| Variables | Odds ratio | p-value | CI 95% |
|---|---|---|---|
| Glycemia | 1.2088 | 0.005 | 1.0589-1.3801 |
| PlGF/Gingival crevicular fluid (pg/ml) | 1.6787 | 0.03 | 1.0512-2.6807 |

TABLE 6

| Variables | Odds ratio | p-value | 95% CI |
|---|---|---|---|
| Glycemia | 1.2059 | 0.023 | 1.0257-1.4177 |
| PlGF/Gingival crevicular fluid (pg/ml) | 1.6795 | 0.03 | 1.0505-2.6851 |
| BMI (kg/m2) | 1.0056 | 0.96 | 0.8094-1.2494 |

TABLE 7

Description of demographic and clinical characteristics of controls (healthy/normotensive patients) and patients with preeclampsia (PE)

| | Healthy/controls patients (n = 20) | | | Pre-eclamptic patients (n = 10) | | |
|---|---|---|---|---|---|---|
| Variables | Mean (SD) | Range | Median (IQR) | Mean (SD) | Range | Median (IQR) |
| Age (years) | 25.65 (6.53) | 18-41 | 24 (9.5) | 26.5 (7.76) | 18-41 | 24.5 (11) |
| Body mass index (BMI) | 28.33 (4.75) | 21.4-41.2 | 28.35 (6.3) | 30.92 (6) | 21.5-42.2 | 30.65 (8.5) |
| Number of teeth | | 18-30 | 27.5 (3) | | 20-28 | 26 (3) |
| Bleeding on probing (BOP) (%) | 42.45 (20.15) | 16.66-94.2 | 37.34 (16) | 58.09 (26.24) | 24.6-99.6 | 55.1 (45.4) |

SD: Standard deviation;
Range: Minimum-maximum values;
IQR Interquartile range

TABLE 8

Association between biomarkers and preeclampsia by logistic regression model crude and adjusted by tobacco use, body mass index and periodontal diagnosis (gingivitis/periodontitis).

| Source | Biomarker | Model* | Odds ratio | p-value |
|---|---|---|---|---|
| Gingival crevicular fluid | PLAP | crude | 1.01 | 0.049* |
| | | adjusted | 1.01 | 0.049* |
| | PlGF | crude | 0.99 | 0.447 |
| | | adjusted | 0.98 | 0.358 |
| | sflt1 | crude | 1.10 | 0.022* |
| | | adjusted | 1.10 | 0.033* |
| | EV-Cd63+ | crude | 1.00 | 0.544 |
| | | adjusted | 1.00 | 0.595 |
| Saliva | PLAP | crude | 1.00 | 0.299 |
| | | adjusted | 1.00 | 0.331 |
| | PlGF | crude | 0.98 | 0.387 |
| | | adjusted | 0.98 | 0.42 |
| | sflt1 | crude | 1.03 | 0.036* |
| | | adjusted | 1.03 | 0.045* |
| | EV-Cd63+ | crude | 1.00 | 0.502 |
| | | adjusted | 1.00 | 0.606 |

The invention claimed is:

1. A method of treating gestational diabetes mellitus, comprising:
   (a) measuring the expression pattern or level of at least placental angiogenic peptide (P1GF), placental alkaline phosphatase (PLAP) or antiangiogenic factor sFlt-1 (sFlt-1) or the concentration levels of extracellular vesicles (EVs), in a gingival crevicular fluid (GCF) sample obtained from a human subject;
   (b) comparing said expression pattern or level of at least placental angiogenic peptide (P1GF), placental alkaline phosphatase (PLAP) or antiangiogenic factor sFlt-1 (sFlt-1) or the concentration levels of extracellular vesicles of the human subject with an already established expression pattern or level; wherein a differential expression of at least placental angiogenic peptide (P1GF), placental alkaline phosphatase (PLAP) or antiangiogenic factor sFlt-1(sFlt-1) or the concentration levels of extracellular vesicles is indicative of gestational diabetes mellitus;

(c) identifying the subject as having gestational diabetes mellitus based on the results of step (b); and (d) treating the subject with a diabetic diet or food plan and/or by administering an oral hypoglycemic drug to the subject.

2. The method of claim 1, wherein the method further comprises:

(a) measuring the expression pattern or level of at least placental angiogenic peptide (P1GF) obtained from a gingival crevicular fluid (GCF) sample of the human subject; and (b) comparing said expression pattern or level of at least P1GF of the human subject with an already established expression pattern or level, wherein overexpression of at least P1GF is indicative of gestational diabetes mellitus.

3. The method of claim 2, further comprising:

(a) measuring the expression pattern or level of at least P1GF and glycemia, or of at least P1GF and PLAP (placental alkaline phosphatase), or of at least PlGF and sFlt-1 (antiangiogenic factor sFlt-1), or of at least P1GF and PLAP and sFlt-1, or of at least P1GF and PLAP and glycemia, or of at least P1GF and sFlt-1 and glycemia, or of at least P1GF and PLAP and sFlt-1 and glycemia, wherein P1GF, PLAP and sFlt-1 are obtained from a GCF sample taken from the subject; and (b) comparing said expression pattern or level of at least P1GF and glycemia, or of at least P1GF and PLAP, or of at least PlGF and sFlt-1, or of at least P1GF and PLAP and sFlt-1, or of at least P1GF and PLAP and glycemia, or of at least P1GF and sFlt-1 and glycemia, or of at least P1GF and PLAP and sFlt-1 and glycemia, of the human subject with an already established expression pattern or level, wherein overexpression of at least P1GF and glycemia, or of at least P1GF and PLAP, or of at least PlGF and sFlt-1, or of at least P1GF and PLAP and sFlt-1, or of at least P1GF and PLAP and glycemia, or of at least P1GF and sFlt-1 and glycemia, or of at least P1GF and PLAP and sFlt-1 and glycemia, is indicative of gestational diabetes mellitus.

4. The method of claim 2 further comprising:

(a) measuring the concentration levels of extracellular vesicles in a gingival crevicular fluid (GCF) sample obtained from the human subject; and (b) comparing said concentration levels with an already established concentration pattern or level, wherein an increased concentration of the concentration levels of extracellular vesicles (EVs) in the sample obtained from the human subject to be screened in comparison to the already established concentration pattern or level, is indicative of gestational diabetes mellitus.

5. The method of claim 2 further comprising confirming the presence of gestational diabetes mellitus by means of an oral glucose tolerance test (OGTT).

6. The method of claim 2, further comprising monitoring the response to the treatment of step (d).

7. The method according to claim 1, wherein the oral hypoglycemic drug is metformin.

8. The method of claim 1, wherein the concentration levels of extracellular vesicles measured in step (a) are exosomes or micro-vesicles.

* * * * *